(12) United States Patent
Walters et al.

(10) Patent No.: US 11,351,355 B2
(45) Date of Patent: Jun. 7, 2022

(54) DEVICES FOR PUMPING BLOOD, RELATED SYSTEMS, AND RELATED METHODS

(71) Applicant: Datascope Corporation, Fairfield, NJ (US)

(72) Inventors: Daniel A. Walters, Rockaway Township, NJ (US); Abraham Ronai, Ridgewood, NJ (US); Wesley Scott Ashton, Bloomingdale, NJ (US); Paul A. Nigroni, Wanaque, NJ (US)

(73) Assignee: DATASCOPE CORPORATION, Wayne, NJ (US)

( * ) Notice: Subject to any disclaimer, the term of this patent is extended or adjusted under 35 U.S.C. 154(b) by 63 days.

(21) Appl. No.: 16/141,652

(22) Filed: Sep. 25, 2018

(65) Prior Publication Data

US 2019/0117865 A1 Apr. 25, 2019

Related U.S. Application Data

(60) Provisional application No. 62/574,707, filed on Oct. 19, 2017.

(51) Int. Cl.
*A61M 60/268* (2021.01)
*A61M 60/135* (2021.01)
(Continued)

(52) U.S. Cl.
CPC ........ *A61M 60/135* (2021.01); *A61M 60/268* (2021.01); *A61M 60/40* (2021.01);
(Continued)

(58) Field of Classification Search
CPC .. A61M 1/125; A61M 1/1043; A61M 1/1096; A61M 1/106; A61M 1/1086;
(Continued)

(56) References Cited

U.S. PATENT DOCUMENTS 3,974,825 A 8/1976 Normann
4,014,317 A 3/1977 Bruno
(Continued)

FOREIGN PATENT DOCUMENTS

WO 96/32971 A1 10/1996
WO 97/02850 A1 1/1997
(Continued)

OTHER PUBLICATIONS

International Search Report and Written Opinion dated Dec. 26, 2018 for corresponding application No. PCT/US2018/056141, 21 pages.

(Continued)

*Primary Examiner* — Ankit D Tejani
*Assistant Examiner* — Joshua Brendon Solomon

(57) ABSTRACT

An intravascular device for pumping blood includes a catheter comprising a membrane chamber located between a proximal end and a distal end of the catheter. An inflatable membrane is disposed within the membrane chamber. The intravascular device includes a first one-way valve and optionally a second one-way valve configured to permit blood flow in a first direction. The first one-way valve may be positioned proximal to the membrane chamber, and the second one-way valve may be positioned distal to the membrane chamber. Methods related to intravascular devices and their respective use are provided.

17 Claims, 10 Drawing Sheets

(51) Int. Cl.
*A61M 60/40* (2021.01)
*A61M 60/50* (2021.01)
*A61M 60/894* (2021.01)

(52) U.S. Cl.
CPC .......... *A61M 60/50* (2021.01); *A61M 60/894* (2021.01); *A61M 2205/3344* (2013.01)

(58) Field of Classification Search
CPC ........ A61M 2205/3344; A61M 60/135; A61M 60/268; A61M 60/894; A61M 60/50; A61M 60/40
See application file for complete search history.

(56) References Cited

U.S. PATENT DOCUMENTS

| | | | |
|---|---|---|---|
| 4,258,717 | A | 3/1981 | Bisera et al. |
| 4,861,330 | A | 8/1989 | Voss |
| 4,906,229 | A | 3/1990 | Wampler |
| 5,092,844 | A | 3/1992 | Schwartz et al. |
| 5,169,378 | A | 12/1992 | Figuera |
| 5,256,141 | A | 10/1993 | Gencheff et al. |
| 5,290,227 | A | 3/1994 | Pasque |
| 5,332,403 | A | 7/1994 | Kolff |
| 5,820,542 | A | 10/1998 | Dobak, III et al. |
| 5,928,132 | A * | 7/1999 | Leschinsky ......... A61M 1/1037 600/16 |
| 6,468,200 | B1 | 10/2002 | Fischi |
| 7,666,131 | B2 | 2/2010 | Weizman et al. |
| 7,914,436 | B1 * | 3/2011 | Kung ................... A61M 1/106 600/18 |
| 7,927,268 | B1 | 4/2011 | St. Germain et al. |
| 8,480,555 | B2 | 7/2013 | Kung |
| 8,932,246 | B2 | 1/2015 | Ferrari |
| 2001/0031907 | A1 | 10/2001 | Downey et al. |
| 2002/0198436 | A1 * | 12/2002 | Hoshino ............. A61M 1/1096 600/18 |
| 2003/0191357 | A1 * | 10/2003 | Frazier .................. A61M 1/101 600/16 |
| 2004/0034272 | A1 * | 2/2004 | Diaz .................... A61M 1/122 600/18 |
| 2004/0059179 | A1 | 3/2004 | Maguire et al. |
| 2006/0199995 | A1 * | 9/2006 | Vijay ............... A61B 17/12022 600/37 |
| 2010/0087773 | A1 * | 4/2010 | Ferrari ................ A61M 1/1096 604/7 |
| 2013/0274645 | A1 | 10/2013 | Ferrari |
| 2016/0136343 | A1 * | 5/2016 | Anagnostopoulos ....................... A61M 1/1005 |
| 2017/0056574 | A1 | 3/2017 | Pfeifer et al. |
| 2017/0173237 | A1 | 6/2017 | Pfeifer et al. |

FOREIGN PATENT DOCUMENTS

| | | |
|---|---|---|
| WO | 2000/41612 A2 | 7/2000 |
| WO | 2010/073890 A1 | 7/2010 |
| WO | 2015/131879 A1 | 9/2015 |
| WO | 2016/034171 A2 | 3/2016 |
| WO | 2019/158420 A1 | 8/2019 |

OTHER PUBLICATIONS

International Preliminary Report on Patentability issued in counterpart International Application No. PCT/US2018/056141, dated Apr. 30, 2020. (12 pages).

Extended European Search Report dated Apr. 22, 2021 in European application No. 18868371.8, 7 pages.

* cited by examiner

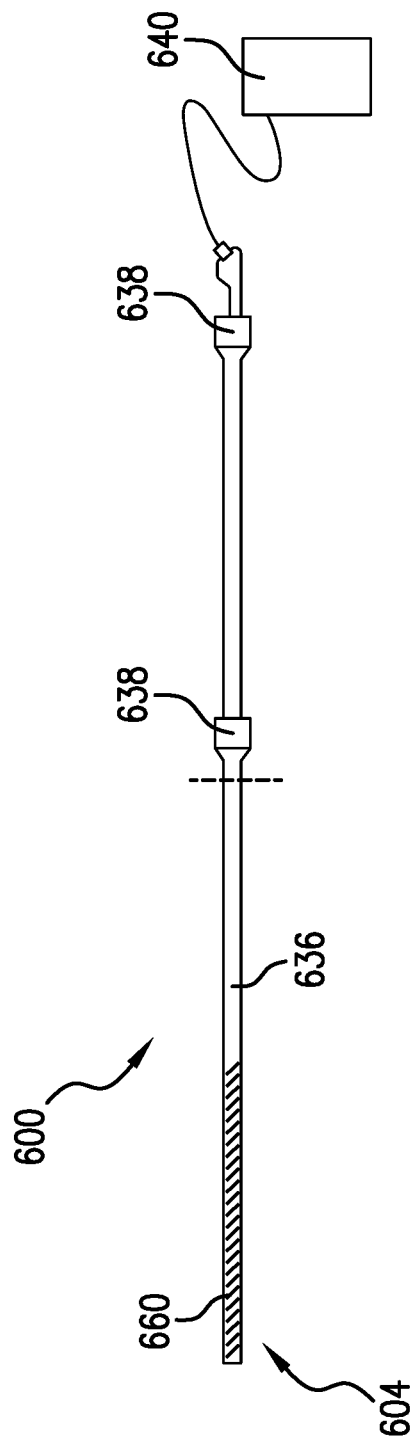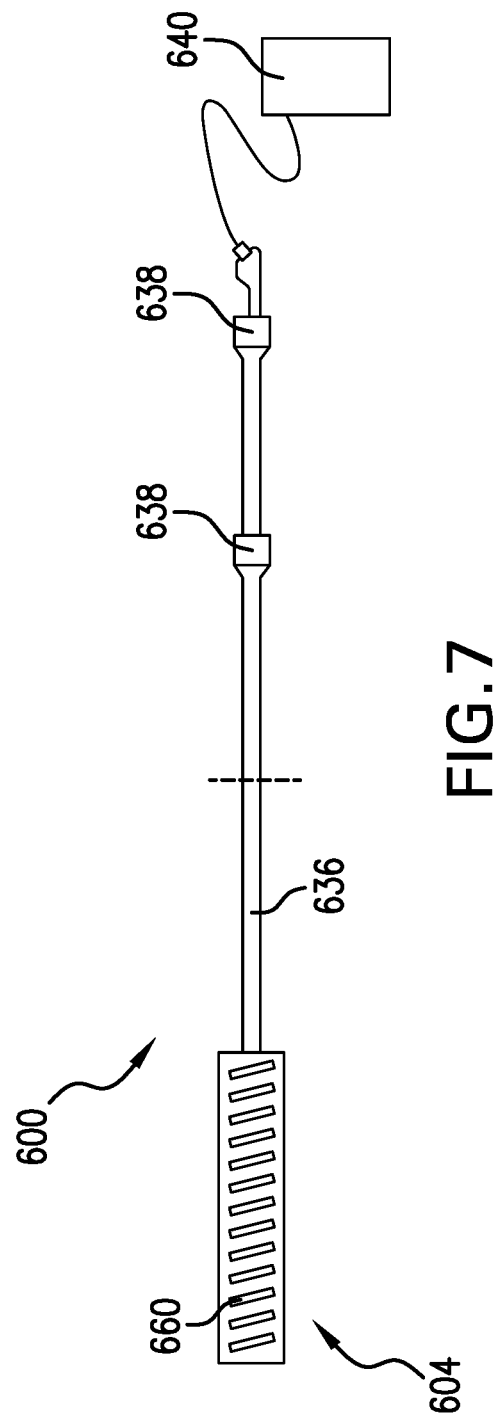

DEVICES FOR PUMPING BLOOD, RELATED SYSTEMS, AND RELATED METHODS

This application claims priority to, and the benefit of, U.S. Provisional Application No. 62/574,707, filed Oct. 19, 2017, and the disclosure of this provisional application is hereby incorporated by reference in its entirety.

TECHNICAL FIELD

The present disclosure relates to intravascular blood pumps such as ventricular assist devices (VADs), and more particularly relates to right ventricular assist devices (RVADs) and left ventricular assist devices (LVADs).

BACKGROUND

One prior art intravascular blood pump is described in U.S. Pat. No. 5,928,132 to Leschinsky, the entire contents of which are incorporated by reference herein. The Leschinsky device includes a catheter with an inflatable balloon positioned within a pumping chamber at or near a distal end of the catheter. The balloon is alternately inflated and deflated by an external pump drive. Deflation of the balloon within pumping chamber of the catheter allows blood to flow into the pumping chamber from the heart. Inflation of the balloon displaces the blood and causes the blood to be expelled from the catheter through outlet valves positioned, for example, on the pumping chamber, thereby supporting the heart. Leschinsky notes that with minor variations, such a device may be used as a right ventricular assist device.

Challenges exist in providing intravascular blood pumping devices that are optimally effective given variations in patient anatomy, such as differences in diameter of aorta or vena cava between patients. Design challenges relate to the need to balance maximizing cannula size for maximum blood flow and reducing cannula size to improve blood flow around and external to the cannula as well as permit smaller profiles for insertion through narrow portions of a patient's vasculature. Further, elements on the cannula itself may reduce or slow blood flow around the cannula. Improvements to device safety and manufacturability are also desired.

SUMMARY

In one aspect of the disclosure, an intravascular device for pumping blood includes a catheter comprising a membrane chamber located between a proximal end and a distal end of the catheter, an inflatable membrane disposed within the membrane chamber, and a valve chamber separate from the membrane chamber. The intravascular device includes a first one-way valve configured to permit blood flow in a first direction.

In another aspect of the disclosure, an intravascular device for pumping blood includes a catheter comprising a membrane chamber located between a proximal tube portion and a distal tube portion. The proximal and distal tube portions each have a profile, when viewed along a lengthwise direction of the device, smaller than the outer profile of the membrane chamber. An inflatable membrane is disposed within the membrane chamber. The intravascular device further includes a first one-way valve associated with a first valve chamber of the catheter, the first valve chamber having a profile, when viewed along a lengthwise direction of the device, smaller than the profile of the membrane chamber.

In yet another aspect of the disclosure, a system for pumping blood includes an intravascular device comprising a catheter comprising a membrane chamber located between a proximal end and a distal end of the catheter, an inflatable membrane disposed within the membrane chamber, and an inlet and an outlet positioned external to and in fluid communication with the membrane chamber. The system further includes a connector assembly configured to connect to the intravascular device and to a pump console and configured to allow settings on the pump console to be altered for use with the intravascular device.

In yet another aspect of the disclosure, a method of forming an intravascular device includes forming at least one valve chamber, the chamber comprising a one-way valve, forming a membrane chamber of an expandable material, the membrane chamber having an expanded configuration and a contracted configuration, coupling at least one valve chamber to the membrane chamber, and coupling a catheter tube to the valve chamber.

In yet another aspect of the disclosure, a method of assisting circulation of blood in a body includes inserting a catheter into a venous structure. The catheter comprises a membrane chamber located between a proximal end and a distal end of the catheter. An inflatable membrane is disposed within the membrane chamber. The catheter includes a first valve chamber forming a portion of or containing a first one-way valve configured to permit blood flow in a first direction, and the first one-way valve is positioned proximal to the membrane chamber. The method further includes positioning the catheter such that the first valve chamber is positioned substantially adjacent to one of a renal vein and a hepatic vein, expanding the membrane chamber from a contracted position to an expanded position, and cyclically supplying a fluid to the inflatable membrane to inflate and deflate the inflatable membrane. Inflation of the membrane permits blood to exit the catheter and deflation of the membrane permits blood to enter the catheter through the first one-way valve.

In yet another aspect of the disclosure, a method of assisting circulation of blood in a body includes inserting a catheter into an arterial structure. The catheter comprises a membrane chamber located between a proximal end and a distal end of the catheter, an inflatable membrane disposed within the membrane chamber, and a first valve chamber forming a portion of or containing a first one-way valve configured to permit blood flow in a first direction. The first valve chamber is positioned proximal to the membrane chamber. The method further includes positioning the catheter such that the first valve chamber is substantially adjacent to a renal artery, expanding the membrane chamber from a contracted position to an expanded position, and cyclically supplying a fluid to the inflatable membrane to inflate and deflate the inflatable membrane, wherein inflation of the membrane permits blood to exit the catheter through the first one-way valve and deflation of the membrane permits blood to enter the catheter.

In accordance with yet another aspect of the present disclosure, an intravascular device for pumping blood includes a catheter comprising a membrane chamber located between a proximal tube portion and a distal tube portion with a distal end. At least one one-way valve is located proximal to or distal to the membrane chamber. The at least one one-way valve is positioned along a length of the device and relative to the distal end such that when the distal end is positioned at a target location relative to a first vascular structure, the at least one one-way valve is positioned adjacent a second vascular structure different from the first vascular structure.

Additional objects, features, and/or other advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

Both the foregoing general description and the following detailed description are exemplary and explanatory only and are not restrictive of the claims; rather the claims should be entitled to their full breadth of scope, including equivalents.

SUMMARY OF THE DRAWINGS

FIG. 6 is a schematic side view of an intravascular device in a collapsed configuration, a deployment-retraction sheath, and a pump device console according to an exemplary embodiment of the disclosure.

FIG. 7 is a schematic side view of the intravascular device, insertion device, and pump device console of the embodiment of FIG. 6 with the intravascular device in an expanded configuration.

DETAILED DESCRIPTION

Figure 1:
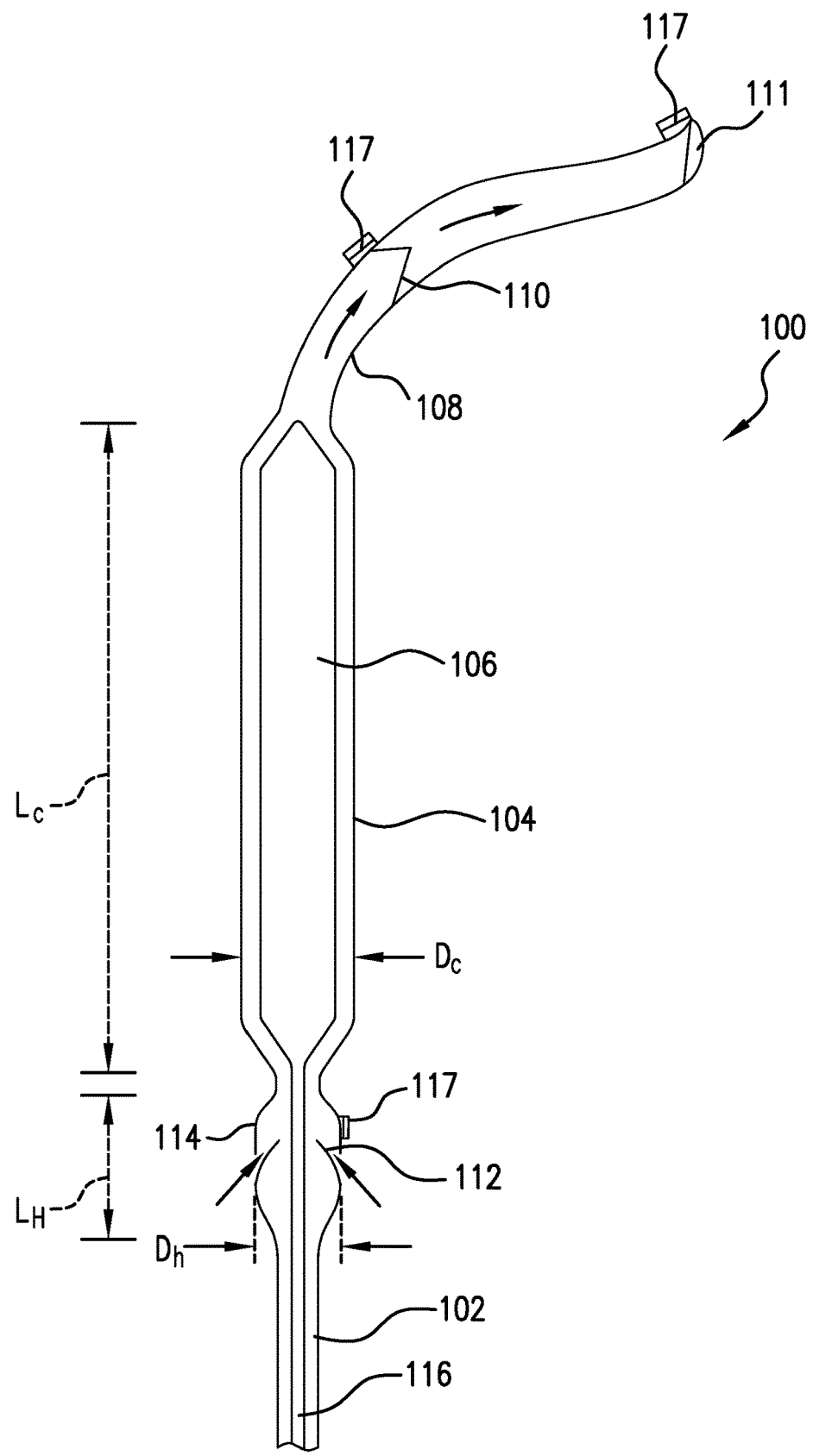
FIG. 1 is a cross-sectional schematic view of a right intravascular device according to an exemplary embodiment of the disclosure.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Further, this description's terminology is not intended to limit the disclosure. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Various exemplary embodiments of the present disclosure contemplate systems, methods, and devices that assist a patient's heart in pumping blood through the left or right heart chambers. In accordance with the present disclosure, an intravascular device (also referred to herein as a device for pumping blood and as a ventricular assist device) comprises a membrane chamber for moving blood into and out of the intravascular device. The membrane chamber contains (or is otherwise configured to receive internally) an inflatable balloon membrane that can be cyclically inflated and deflated to move blood into and out of the intravascular device through inlet and outlet valves of the device. In accordance with one aspect of the present disclosure, the intravascular devices may be configured to reduce (e.g., minimize) interference between anatomical structures of the patient and inlet and/or outlet valves of the intravascular device. For example, in certain exemplary embodiments, the valves may be located on portions of the intravascular device that have an outer diameter less than a maximum outer diameter of the membrane chamber containing the balloon membrane of the intravascular device. Locating the valves off the membrane chamber serves several purposes, permitting maximum flow around the device within a blood vessel while also permitting the valves to open to their full extent, to maximize inflow and outflow of blood through the membrane chamber. In addition, the size of the membrane chamber need not be limited by the need for valves on the chamber to open, thus allowing the size of the membrane chamber to be maximized. Stated another way, the size of the membrane chamber is limited when valves are located on the membrane chamber, because the chamber must be small enough to allow the valves to open without contacting the surrounding blood vessel. While this disclosure provides several embodiments in which all valves are located off the membrane chamber, it is within the scope of the present disclosure to include one or more valves on the membrane chamber as well, as will be discussed with respect to the exemplary embodiment of FIG. 11 below. In such an embodiment, it may be desirable to locate the valve(s) on the chamber in such a way that the size of the membrane chamber need not be limited to permit the valves to fully open.

Locating the valves off the membrane chamber may also increase ease of manufacturing of the device. In certain exemplary embodiments, the valves may be positioned in valve chambers separate from the membrane chamber. In certain embodiments, the membrane chamber is valveless, meaning that there are no valves formed in the membrane chamber, or in any sidewall of the membrane chamber, or on any sidewall of the membrane chamber. The valve chamber may comprise a volume in fluid communication with the membrane chamber as well as other portions of the catheter. The valve chamber may take several different forms. For example, the valve chamber may be a part of one or both of a proximal or distal tube portion of the catheter. In such an embodiment, the portion of the proximal or distal tube may be expanded or ballooned to have a diameter that is larger than the remaining portion of the proximal or distal tube, and a one-way valve, such as an inlet or an outlet valve, may be positioned within the expanded or ballooned portion of the tube (i.e., in the valve chamber). In another exemplary embodiment, the valve chamber may take the form of an inlet tube or an outlet tube. The inlet tube or outlet tube may contain an inlet valve or outlet valve, respectively, placed into fluid communication with the membrane chamber, with the inlet tube or outlet tube extending substantially in parallel with proximal or distal tube portions of the catheter. Additionally, or alternatively, the valve chamber may take the form of a separate valve assembly that includes a valve chamber containing one or more valves, such as inlet valves or outlet valves, and the valves may include respective valve housings, or may be housed by a common housing. In such a case, the valve assemblies may be manufactured separately from other portions of the intravascular device, such as the membrane chamber and tubes, and may be coupled with the other portions of the intravascular device to form the complete intravascular device. The valve chamber may take on other configurations which place the valve(s) contained therein in fluid communication with the membrane chamber, as will be apparent to those of skill in the art.

Figure 3:
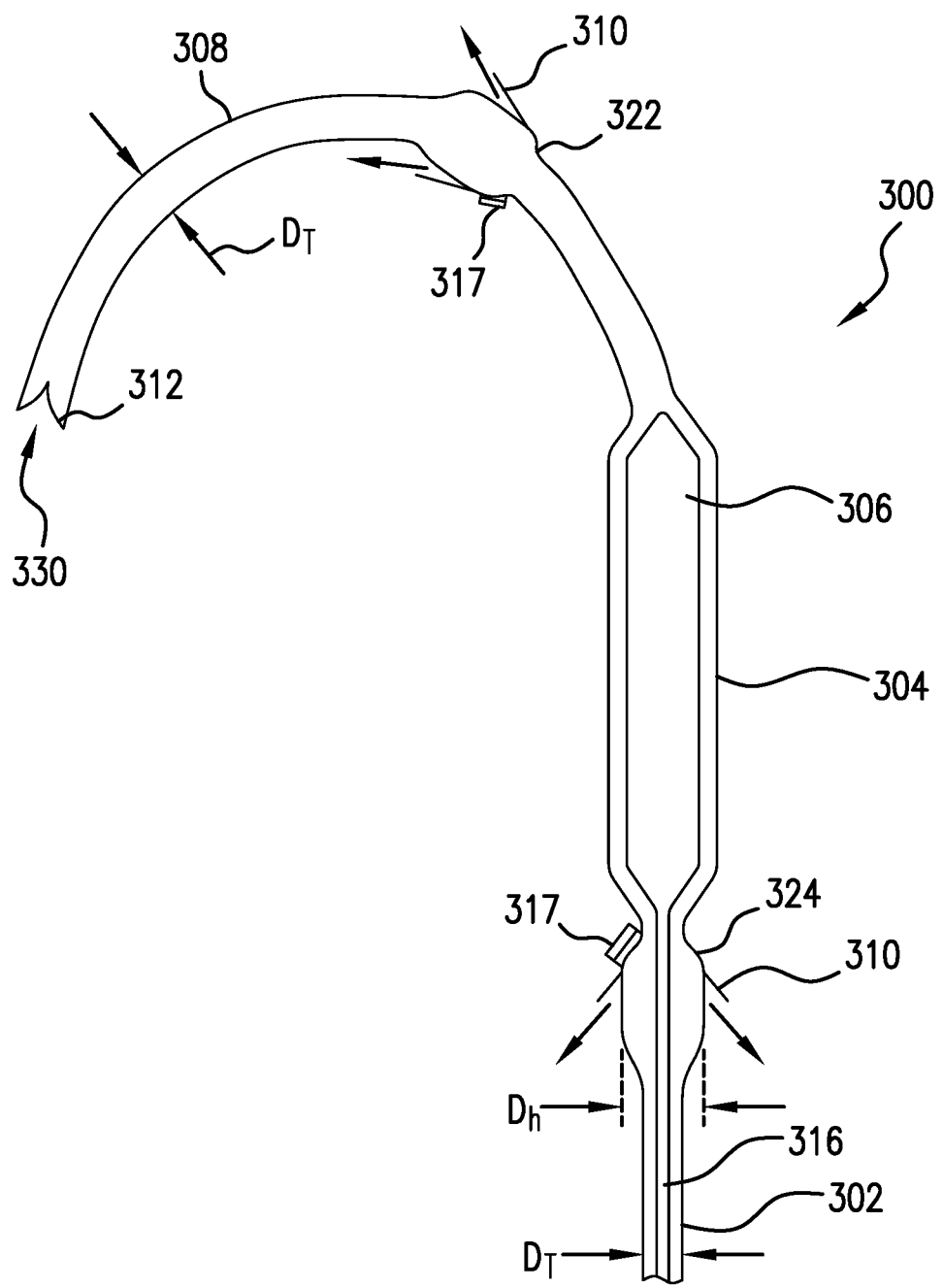
FIG. 3 is a cross-sectional schematic view of a left intravascular device according to yet another exemplary embodiment of the disclosure.
Figure 4:
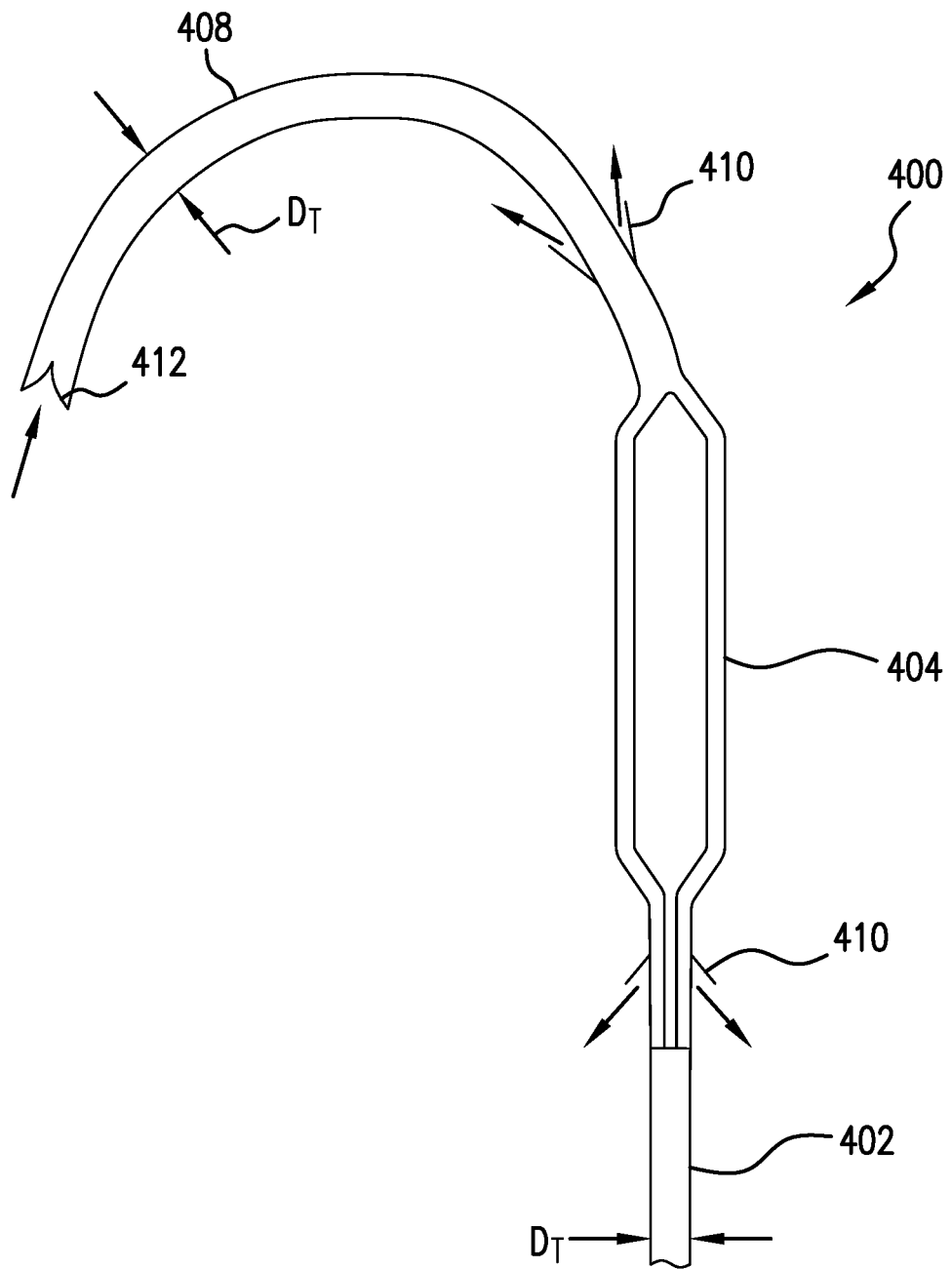
FIG. 4 is a cross-sectional schematic view of a left intravascular device according to yet another exemplary embodiment of the disclosure.

Utilizing valve subassemblies in the device, in addition to improving manufacturability, also allows for a level of customization of the device. That is, the valve subassemblies can be located to accommodate variations in patient anatomy and can be located to direct blood flow to preferred anatomical areas. For example, in accordance with another aspect of the present disclosure, the inlet and/or outlet valves of the intravascular device may be positioned to optimally supply flow to various anatomical locations, such as to provide or otherwise cause improved (e.g., optimal) cerebral and/or renal perfusion. For example, in some exemplary embodiments of the disclosure, the intravascular device may include multiple outlet valve locations. For example, as illustrated in FIGS. 3 and 4, an intravascular device in accordance with the present disclosure may include a first outlet valve located distal to or proximal to the membrane chamber. Optionally, the intravascular device may have a second outlet valve located proximal to the membrane chamber (when the first outlet valve is located distal to the membrane chamber) or distal to the membrane chamber (when the first outlet valve is located proximal to the membrane chamber). Additionally, in other exemplary embodiments of the device, the intravascular device may include multiple inlet locations. For example, an intravascular device in accordance with the present disclosure when adapted for a right heart support application may include a first inlet valve located on the device to be positioned adjacent a hepatic vein and a second inlet valve located on the device to be positioned adjacent a renal vein. Both inlet valves in such a configuration may be located proximal to the membrane chamber, and the intravascular device may have an outlet located at its distal end region. Alternatively, or additionally, one of the inlet valves may be located on the membrane chamber as shown in the exemplary embodiment of FIG. 11.

In accordance with another aspect of the present disclosure, the intravascular device may include features configured to interface with a console of a pump drive that supplies a flow of working fluid (such as a gas) to alternately inflate and deflate the balloon membrane within the membrane chamber (i.e., the balloon membrane housing). For example, in some exemplary embodiments, the intravascular device includes a transducer such as a pressure transducer that is configured to provide a pressure signal to the pump drive. The pressure signal may be used to control aspects of the pump drive action, such as timing of inflation and deflation cycles, dwell times at an inflated or deflated state, or other aspects of the pump drive action. Additionally, or alternatively, the pressure signal may be used to provide pressure information at a user interface of the pump drive console. Other transducers such as sound transducers may be utilized instead of or in addition to a pressure transducer to be used to control aspects of the pump drive action.

The console of the pump drive may include various pre-programmed pumping algorithms which may be selected to provide optimized pumping action based on parameters such as the type of intravascular device being used, certain aspects of the patient's anatomy, and the patient's response to assist treatment, and other factors such as the patient's hemodynamics before therapy, the degree of valvular insufficiency, and the patient's response to other therapies. Additionally, the console of the pump drive may be configured to enable a practitioner to manually set aspects of the pumping action based on, for example, factors such as those above. In some exemplary embodiments, the intravascular device may include an identification device that provides information regarding operating characteristics of the intravascular device to the pump drive console to enable the pump drive console or the practitioner to choose suitable operating parameters for the pumping action. In accordance with one aspect of the present disclosure, connection to the identification device may cause the pump console to display a user interface configured for the intravascular device. For example, connection with the identification device may cause a display on the pump console to automatically change from operational settings for a first operational mode to a second operational mode that includes operating settings for use with an intravascular device. The types of settings for an intravascular device that might be displayed and controlled through the pump console may relate to, for example, alarm settings, detection settings, alarm conditions, device cycle triggering, device cycle timing, and user interface settings. In certain embodiments, the identification device is a radio-frequency identification (RFID) device incorporated into the intravascular device.

Referring now to FIG. 1, an exemplary embodiment of an intravascular device 100 is shown. In the embodiment of FIG. 1, the intravascular device 100 is configured to support the right heart, and therefore may be referred to as a right ventricular assist device ("RVAD"). The intravascular device 100 comprises a membrane chamber 104. A membrane or diaphragm or balloon that is configured to expand and contract (or inflate and deflate or otherwise change the occupied volume in the membrane chamber 104) is positioned within the membrane chamber to provide the pumping function. Such membranes or diaphragms may be referred to interchangeably herein as expandable or inflatable membranes or balloon membranes or intra-aortic balloons (IABs) (although it is anticipated to also use a balloon member other than that used on an IAB). These membranes may be formed, for example, from polymers or other flexible materials. As non-limiting examples, the membranes may comprise polyurethane, silicone, or other polymers. Further examples of membranes and materials they may incorporate may be found in U.S. Pat. No. 6,482,173, issued on Nov. 19, 2002, the entire contents of which are incorporated by reference herein. Additionally, in certain embodiments the balloon may be distensible and in other embodiments the balloon may be non-distensible. In the exemplary embodiment of FIG. 1, an inflatable membrane balloon 106 used in intra-aortic balloon (IAB) devices, is positioned within membrane chamber 104. A tube 102 is in fluid communication with and extends proximally from membrane chamber 104. The tube 102 may be referred to as a proximal tube portion. As used herein, the term "proximal" refers to a direction along the intravascular device 100 toward an end of the device that remains outside the patient's body and is connected to external equipment such as a pump console 640 (shown in FIGS. 6 and 7), and the term "distal" refers a direction along the intravascular device 100 toward an end of the device opposite the proximal end, such as a free end of the device being configured for placement within patient's right or left heart. The tube 102 may extend all the way out of the patient, e.g., to the pump console 640, or the tube 102 may not extend out of the patient and may seal against the outer surface of tube 116 to prevent blood leakage during pumping.

A tube 108 is in fluid communication with and extends distally from membrane chamber 104 and includes an outlet valve 110 and an open distal end 111. The tube 108 may be referred to as a distal tube portion. In an exemplary embodiment, the outlet valve 110 may be a one-way valve, such as a check valve, that opens or closes based on relative pressures present on either side of the outlet valve 110. In some exemplary embodiments, the tube 108 may have a "J" shape or be coupled to a "J" shaped extension or pigtail. Such a configuration may prevent the open distal end 111 from becoming occluded by vascular walls when in position within a patient. Extensions having such configurations are shown in, for example, U.S. Patent App. Pub. No. US2010/0268017 A1 to Siess, published on Oct. 21, 2010, and U.S. Pat. No. 9,545,468 to Aboul-Hosn, granted Jan. 17, 2017, the entire contents of each of which are incorporated by reference herein. An inlet valve 112 is disposed in an inlet valve chamber 114 located between and in fluid communication with the tube 102 and the membrane chamber 104. Similar to the outlet valve 110, in an exemplary embodiment, the inlet valve 112 may be a one-way valve such as a check valve that operates based on a pressure differential on either side of the inlet valve 112. The inlet valve 112 and inlet valve chamber 114 may be referred to as a valve subassembly. In some exemplary embodiments, the inlet valve 112 may be disposed directly on the tube 102, or on an expanded portion of the tube 102. In an exemplary embodiment, the inlet valve 112 may comprise one or more film flaps connected at one end to the inlet valve chamber 112 or tube 102. In other exemplary embodiments, the valve 112 may comprise a flapper valve, a duckbill valve, or other valve configurations.

The membrane balloon 106 is connected to an external fluid supply, such as a supply of shuttle gas from a pump console 640 (shown in connection with FIGS. 6 and 7) that alternatingly inflates and deflates the membrane balloon 106 within the membrane chamber 104. As a non-limiting example, the gas supplied may be helium to prevent formation of an embolism in the event the gas escapes from the intravascular device 100 and into the patient's bloodstream. As will be understood by those of ordinary skill in the art, other appropriate gasses or fluids may be used to inflate the membrane balloon 106. The gas may be supplied through a shaft 116 of the device that is in fluid communication with the membrane balloon 106 and that passes through the tube 102 and receives the supply of gas from the pump console 640.

In use, the membrane chamber 104 of the device is in a compressed or contracted configuration prior to insertion, to reduce the overall profile of the device and allow for percutaneous insertion. For right-heart circulatory support, the device may be inserted into the right subclavian vein to access the superior vena cava, the right atrium, or right ventricle. Additionally, the femoral vein may be used to access the inferior vena cava, right atrium, or right ventricle when used for right-heart circulatory support. For left-heart support, the left femoral artery may be used to access the aorta. While various embodiments of the disclosure are described herein in terms of percutaneous insertion, the disclosure contemplates insertion in other ways, such as direct aortic insertion or surgical cut-down insertion. The membrane chamber (and other portions of the device) may incorporate, for example, a self-expanding material to move from the contracted configuration to the expanded configuration on its own after insertion into and positioning within the blood vessel. Examples of such structures include for example those disclosed in U.S. Patent App. Pub. No. US2012/0172655 and PCT publication WO2012094525 to Campbell et al., as well as those disclosed in PCT publication WO2013173245 to Zeng et al., the entire contents of each publication are incorporated by reference herein. Examples of materials that may be used for such self-expanding structures include shape memory materials. As non-limiting examples, such shape memory materials may include shape-memory alloys (SMAs) such as nitinol (NiTi), Fe—Mn—Si, Cu—Zn—Al, Cu—Al—Ni, or other SMAs, and shape memory polymers (SMPs), such as polyurethane-based, polystyrene-based, cyanate ester-based, and epoxy-based SMPs. Alternatively, a compressible material having sufficient "spring back" (i.e., a material having a sufficiently high elastic modulus) to expand after being compressed for insertion may be used. Examples of suitable materials include, for example, stainless steel or other metals or metal alloys, or polymers such as polyimide or polyether ether ketone (PEEK). In such an embodiment, it may be desirable to use a sheath or other sleeve like member to maintain the membrane chamber in a compressed configuration during insertion. The sheath can be withdrawn after placement of the device. As another alternative, the material used may not be self-expandable. In such a case, expansion and retraction of the membrane chamber may occur through other mechanical methods such as, for example, those disclosed in U.S. Pat. No. 4,444,186, which is incorporated herein by reference in its entirety. With the membrane chamber in a compressed or contracted configuration, the distal end 111 of the device is inserted percutaneously through an incision in the patient's body and into an arterial or venous structure such as, for example, the femoral artery or the femoral vein. As will be understood by those of ordinary skill in the art, other insertion sites such as axillary, subclavian, or brachiocephalic arteries or veins may be used, depending upon the specifics of the device and patient. The exemplary embodiment shown in FIG. 1 is a RVAD configured to assist in moving blood from the vena cava, the right atrium, or the right ventricle to the lungs via the pulmonary artery and/or across the heart, and in an exemplary use, the device may be inserted through the femoral vein and guided into the inferior vena cava (IVC) with the distal end 111 of the outlet tube 108 positioned to provide outlet flow from the outlet valve 110 to the patient's pulmonary trunk. The inlet valve chamber 114 may be positioned in the IVC, the right atrium, or the right ventricle. In other exemplary embodiments, the device may be inserted through the superior vena cava, depending on the specific therapeutic needs of the patient and factors related to the patient's anatomy. When the balloon is in a deflated state, blood pressure in the vena cava, the right atrium, or the right ventricle, depending on where the inlet valve chamber 114 is positioned, causes the inlet valve 112 to open and allow blood to flow into the membrane chamber 104 around the deflated membrane balloon 106. The outlet valve 110 remains closed while the membrane chamber 104 fills with blood. Once the membrane chamber 104 is filled, inflation of the membrane balloon 106 causes the pressure to rise in the membrane chamber 104 above the pressure in the right atrium or ventricle, causing the inlet valve 112 to close, thereby preventing retrograde flow of blood due to balloon inflation. Pressure in the membrane chamber 104 causes the outlet valve 110 to open, and blood is expelled from the membrane chamber 104, through the outlet tube 108, and into the pulmonary artery. In this manner, the intravascular device 100 assists the right heart in pumping blood from the vena cava, right atrium, or right ventricle to the pulmonary artery.

Various configurations of the inlet valve 112 and outlet valve 110 are possible, including such configurations in which the outlet valve 110 is not present. For example, in the exemplary embodiment of FIG. 1, the inlet valve 112 is contained within the inlet valve chamber 114. The inlet valve chamber 114 and inlet valve 112 may be manufactured as a separate assembly from the membrane chamber 104, and may be coupled to the membrane chamber 104 and the tube 102 to form the intravascular device 100. For example, an assembly of the inlet valve chamber 114 and the inlet valve 112 may be coupled with the membrane chamber 104 or tube 102 by bonding using, e.g., adhesives, welding such as ultrasonic, friction, or laser welding, or any other method. The valve chamber 114 may, in certain embodiments, be formed as a dilated or ballooned portion of the tube 102 as described below. Forming the inlet valve assembly separate from the membrane chamber 104 affords flexibility in manufacturing the inlet valve assembly and the membrane chamber. For example, in some exemplary embodiments, manufacturing or bonding elements of the valves to other components of the device involves thermal or chemical processes. By manufacturing the valve assembly separate from other components of the device, adverse effects of such thermal or chemical processes on other components of the device may be reduced or eliminated.

Additionally, manufacturing the valve chamber 114 separate from the membrane chamber 104 provides additional flexibility regarding the position of the valves relative to the membrane chamber 104. For example, the longitudinal position of the valve assembly relative to the membrane chamber 104 can be changed by, for example, including a tube of desired length between the membrane chamber 104 and the valve assembly (as shown and discussed in connection with the exemplary embodiment of FIG. 3). In this way, the position of the valves may be tailored to improve (e.g., optimize) the efficacy of the intravascular device by positioning the valves in locations that improve perfusion of blood to anatomical structures and, alternatively or additionally, reduce the tendency of anatomical structures to partly or fully occlude the valves.

As an exemplary alternative to providing a separate chamber for the valve 114, the inlet valve chamber 114 may be formed by expanding a portion of the tube 102 to form the inlet valve chamber 114. For example, a portion of the tube 102 could be expanded by heating and pressurizing the tube 102 within a mandrel that molds the tube 102 to the desired shape, by swaging the tube 102, or by any other method. As a further non-limiting example, the inlet valve chamber 114 may be formed as a reduced-diameter tube in fluidic communication with the membrane chamber 104, which is mechanically or chemically bonded to the tube 102.

An outer lateral dimension of the inlet valve chamber 114 may be less than a corresponding outer lateral dimension of the membrane chamber 104. The lateral dimension may also be referred to as a profile dimension, or an outer profile. The profile may refer to the profile of the membrane chamber 104 as viewed along a lengthwise direction of the device. For example, the inlet valve chamber 114 may have an outer diameter Dh that is less than an outer diameter Dc of the membrane chamber 104. The diameter Dh of the inlet valve chamber 114 may be greater than an outer diameter DT of the outlet tube 108 and proximal tube 102. The reduced outside diameter of the intake valve chamber 114 relative to the diameter Dc of the membrane chamber 104 may facilitate operation of the valves without occlusion by anatomical structures. For example, because the inlet valve chamber 114 diameter Dh is less than diameter Dc of the membrane chamber 104, when the membrane chamber 104 is in position within a patient's heart, the smaller diameter Dh of the inlet valve chamber 114 may provide clearance between anatomical walls and the inlet valve 112, thereby potentially avoiding occlusion of the inlet valve 112. This also allows for increased blood flow within the blood vessel and around the membrane chamber 104. Also, the smaller diameter of the inlet valve chamber 114 presents less of an obstruction and decreases the resistance to blood flowing around the outer surfaces of the intravascular device 100 than if the inlet valve chamber 114 and the membrane chamber 104 had the same diameter when fully deployed or expanded. Further, although optional outlet valve 110 is shown contained within tube 108 in FIG. 1, the present disclosure contemplates that outlet valve 110 may also be contained within a housing separate from the tube 108, or formed in an expanded portion of the tube 108. While the outer lateral dimensions of the membrane chamber 104, the inlet valve chamber 114, and the tubes 102 and 108 are discussed in terms of diameter, the membrane chamber 104, the inlet valve chamber 114, and the tubes 102 and 108 are not limited to having a circular cross-section. For example, a cross section of the membrane chamber 104, the inlet valve chamber 114, the tube 102, and/or tube 108 may be, as non-limiting examples, ovoid, square, rectangular, or have other polygonal or non-polygonal shapes.

As shown in FIG. 1, the membrane chamber 104 comprises a length LC, and the inlet valve chamber 114 comprises a length LH. The length LC of the membrane chamber 104 may be greater than the length LH of the inlet valve chamber 114. Additionally, the membrane chamber 104 may comprise an interior volume defined by interior shape and dimensions of the membrane chamber 104. The inlet valve chamber 114 may comprise an interior volume defined by the interior shape and dimensions of the inlet valve chamber 114. The interior volume of the membrane chamber 104 may be greater than the interior volume of the inlet valve chamber 114.

In some exemplary embodiments, the intravascular device 100 may include markers 117 positioned adjacent the inlet valve 112 and the end of the outlet tube 108 to aid a practitioner in positioning the intravascular device 100 so that the valves are located optimally for effective uptake and perfusion of blood. The markers 117 may comprise a radiopaque material that is visible in x-ray and under fluoroscopy, such as a halogen or metallic compound. Non-limiting examples of such radiopaque materials include tungsten, tantalum, or BaSO4 (barium sulfate).

In some exemplary embodiments, portions of the intravascular device 100 may include an anti-thrombogenic coating to reduce the occurrence of thrombi formation. Such a coating may be applied to the entire intravascular device 100, or only portions of the intravascular device 100, such as in, on and/or near the valve chambers, the membrane chamber 104, etc. The coating may be applied to the exterior and/or interior of the device. The coating may be an immobilized heparin coating formed by alternating layers of albumen and heparin, or may include other combinations of heparin and/or albumen. One example of such an immobilized heparin coating is BIOLINE®, available from Maquet Cardiovascular, LLC, 45 Barbour Pond Drive, Wayne, N.J., 07470 USA.

Figure 2:
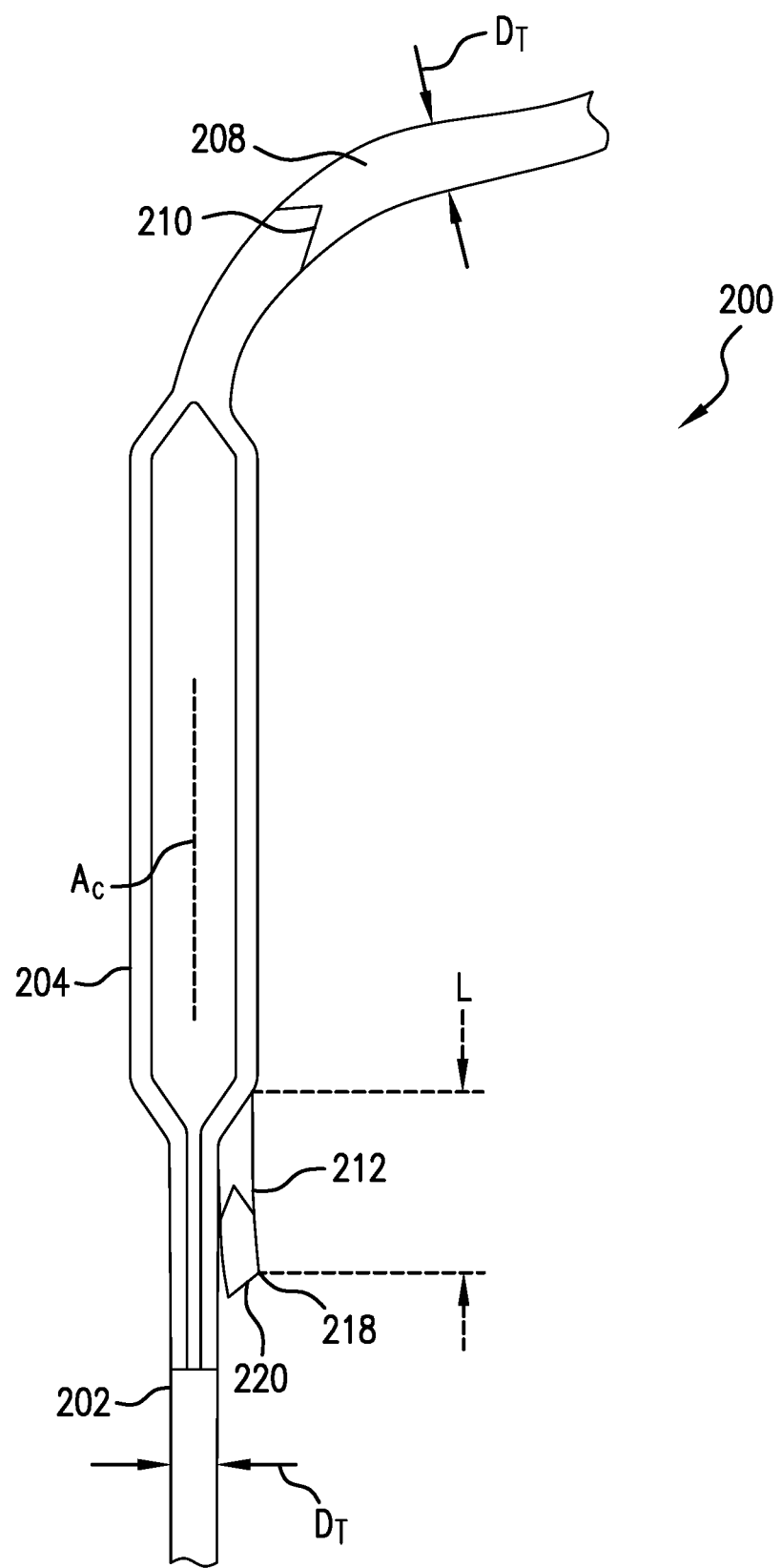
FIG. 2 is a cross-sectional schematic view of a right intravascular device according to another exemplary embodiment of the disclosure.

In some embodiments, the inlet valve chamber may comprise an inlet tube with an open end and an inlet valve positioned within the inlet tube. For example, referring now to FIG. 2, an intravascular device 200 includes an inlet tube 218 with an open end 220 and an inlet valve 212 disposed in the inlet tube 218. The intravascular device 200 also includes an outlet tube 208 with an outer diameter DT and an outlet valve 210 within the outlet tube 208. In the exemplary example of FIG. 2, the inlet tube 218 is coupled with a membrane chamber 204, and the inlet tube 218 is positioned offset from a central axis Ac of the membrane chamber 204, and a tube 202 is positioned coaxial with the central axis Ac of the membrane chamber 204. In other embodiments, the tube 202 may be offset relative to the central axis Ac, and the inlet tube 218 may be positioned coaxial with, or offset relative to, the central axis Ac of the membrane chamber 204.

The inlet tube 218 may have an outer diameter DT, and a length L chosen to position the open end 220 of the inlet tube 218 in an optimal position for drawing blood into the membrane chamber 204 from the anatomical structure in which the intravascular device is positioned. Similar to the embodiment of FIG. 1, the configuration of the inlet tube 218, such as the length L, may be chosen to avoid occlusion of the open end 220 of the inlet tube 218 by anatomical structures of the patient.

Referring now to FIG. 3, another exemplary embodiment of an intravascular device 300 is shown. In the embodiment of FIG. 3, the intravascular device 300 is configured to support the left heart, and may be referred to as a left ventricular assist device ("LVAD"). The intravascular device 300 includes a membrane chamber 304 containing a membrane balloon 306 configured to communicate with a pump console (e.g., pump device console 640 shown in FIGS. 6 and 7). An inlet tube 308 extends from a distal portion of the membrane chamber 304, and includes an inlet valve 312 located at a location distal to the membrane chamber, such as at open end 330 of the inlet tube 308. The intravascular device includes first and second outlet valve chambers 322 and 324, each chamber may be provided with a housing including an outlet valve 310. The first outlet valve chamber 322 is positioned distal to the membrane chamber 304 and proximal to the inlet valve 312, and the second outlet valve chamber 324 is positioned proximal to the membrane chamber 304.

As with the inlet valve chamber 114 discussed in connection with the embodiment of FIG. 1, the outlet valve chambers 322 and 324 may be manufactured separately from the membrane chamber 304 and then attached to the membrane chamber 304, as is the outlet valve chamber 324 in the exemplary embodiment of FIG. 3, or attached to the membrane chamber 304 by a portion of the inlet tube 308, as shown in the exemplary embodiment of FIG. 3 with respect to outlet valve chamber 322. Alternatively, the outlet valve chambers 322, 324 may be formed by expanding a portion of the tube 308, and positioning the outlet valves 310 in the expanded portion of the tube 308. Positioning multiple outlet valve chambers (e.g., outlet valve chambers 322 and 324) along the length of the intravascular device 300 may enable blood flow to be directed to specific areas to optimize perfusion, e.g., cerebral and renal perfusion of blood from the intravascular device 300. For example, in the embodiment of FIG. 3, the outlet valve chambers 322 and 324 are configured to be positioned adjacent the common carotid artery and the renal arteries. Although the embodiment of FIG. 3 is illustrated with two outlet valve chambers, it is within the scope of this disclosure to provide additional valve chambers either proximal and/or distal to the membrane chamber depending upon a physiologic need.

Similar to the inlet valve chamber 114 discussed in connection with the embodiment of FIG. 1, the outlet valve chambers 322 and 324 have an outside diameter Dh that is less than the outer diameter Dc of the membrane chamber 304. Such a configuration may prevent interference with or occlusion of the outlet valves 310 when the intravascular device is positioned with the anatomical structure, particularly in configurations where the outlet valves 310 open outward, as shown in FIG. 3. This also allows for increased blood flow within the blood vessel and around the membrane chamber 304. Further, although inlet valve 312 is shown contained within the end of tube 308 in FIG. 3, the present disclosure contemplates that inlet valve 312 may also be contained within a chamber. Further, the present disclosure also contemplates that the outer diameter Dh of chambers 322 and 324 may be greater than an outer diameter DT of tubes 302 and 308. Additionally, in some embodiments, the outer diameter Dh of the chambers (such as chambers 322 and 324) may be greater than an outer diameter Dc of the membrane chamber 304.

In use, the membrane chamber 304 of the device is in a compressed or contracted configuration prior to and during insertion, to reduce the overall profile of the device and allow for percutaneous insertion. Additionally, one or both of the tubes 302 and 308 may be introduced in a furled (i.e., reduced diameter) state to reduce the overall diameter of the device to facilitate insertion. The membrane chamber (and other portions of the device) may incorporate, for example, a self-expanding material to move from the contracted configuration to the expanded configuration on its own after insertion into and positioning within the blood vessel. Examples of such self-expanding materials include shape memory materials such as the SMAs and SMPs listed above in connection with the embodiment of FIG. 1. Alternatively, a compressible material having sufficient "spring back" to expand after being compressed for insertion may be used. Examples of suitable materials include materials exhibiting high elastic moduli, such as the materials listed above in connection with the embodiment of FIG. 1. In such an embodiment, it may be desirable to use a sheath or other sleeve like member to maintain the membrane chamber in a compressed configuration during insertion. The sheath can be withdrawn after placement of the device. As another alternative, the material used may not be self-expandable. In such a case, expansion and retraction of the membrane chamber may occur through other mechanical methods such as, for example, those disclosed in U.S. Pat. No. 4,444,186, which is incorporated herein by reference in its entirety, and by those disclosed in U.S. Pat. No. 5,928,132, which is also incorporated herein by reference. With the membrane chamber in a compressed or contracted configuration, the intravascular device 300 may be percutaneously inserted through a patient's femoral artery, for example, until the inlet tube 308 is positioned in the patient's left ventricle and the outlet valve chambers 322 and 324 and the membrane chamber 304 are positioned within the patient's aorta. As previously noted, one or more of the outlet valve chambers may have markings, such as radiopaque markers 317, that allow the housings to be viewed during insertion via fluoroscopy. This permits the surgeon to adjust and then observe position of one or both of the outlet valves to maximize perfusion, for example, cerebral perfusion or renal perfusion. This application also contemplates that the markers may be positioned near to or adjacent to the valves and not always on the valve chambers. For example, markers may be positioned on tubing immediately proximal or immediately distal to a valve chamber.

The shaft 316 connects membrane balloon 306 to pump console 640 (FIGS. 6 and 7) to allow cyclical inflation of balloon membrane 306 with gas or other fluid supplied by pump console 640 to inflate and deflate balloon membrane 306. In use, when the membrane balloon 306 is in a deflated state, blood pressure in the left ventricle causes the inlet valve 312 to open, and blood enters the membrane chamber 304 through tube 308. When the membrane balloon 306 is inflated, the increased pressure in the membrane chamber 304 causes the inlet valve 312 to close to prevent retrograde flow through the opening 330, and blood is expelled from the membrane chamber 304 through the outlet valves 310.

In addition to tailoring the position of each of the outlet valves 310 to increase (e.g., maximize) perfusion of blood to particular anatomical structures, the flow rates of each of the outlet valves 310 may make up a different proportion of a total flow rate from the intravascular device 300. For example, an outlet valve positioned farther from the membrane chamber 304 may have a lower flow rate as compared to an outlet valve positioned closer to the membrane chamber 304 due to losses (e.g., frictional factors) in the tube 308. Additionally, different outlet valves 310 may have different flow areas (e.g., cross sectional areas) to provide different overall flow rates as between different valves. For example, the outlet valves 310 may be configured so that half of the pumping volume goes through the proximal valve and half of the pumping volume goes through the distal valve. However, depending upon estimated needs for a patient, the split in total flow volume to proximal and distal outlet valves 310 may be divided 60:40, 70:30, 40:60 or 30:70, if desired, depending upon valve configuration and desired perfusion strategies. As a non-limiting example, the flow rate adjacent to the renal arteries may be made larger than the flow rate adjacent to the common carotid, brachiocephalic and subclavian arteries if such an arrangement would be beneficial to patient recovery. Alternatively, to ensure appropriate flow to the upper branches of the aorta, the flow rate of the device may be made larger in that area. FIG. 4 shows a left intravascular device 400 similar to the intravascular device 300 of FIG. 3. In the embodiment of FIG. 4, outlet valves 410 are proximal to a membrane chamber 404 and an inlet tube 408, and distal to a proximal tube 402 having an outer diameter DT. The inlet tube 408 has an outer diameter DT and extends distally from the membrane chamber 404 and includes an inlet valve 412 and another outlet valve 410. The potential for interference with or occlusion of the outlet valves 410 by anatomical structures when the intravascular device is positioned within a patient's body is reduced by locating the outlet valves 410 in portions of the intravascular device having a smaller outer diameter than the outer diameter of the membrane chamber 404. In the embodiment of FIG. 4, the outlet valves 410 are incorporated into a structure of the device 400 having an outer diameter similar or equal to the outer diameter DT of the inlet tube 408 and the proximal tube 402. For example, the outlet valves 410 may be located within valve chambers (not shown in FIG. 4) similar to the embodiment of FIG. 3, or the outlet valves 410 could be located within expanded portions of the tube 402 or inlet tube 408. The outlet valves 410 located distal to the membrane chamber 404 are in a more proximal location as compared to the analogous outlet valves 310 shown in FIG. 3. Such differing valve placement may facilitate perfusion to different areas of the patient's anatomy compared to the embodiment of FIG. 3, or may be tailored to compensate for differences in anatomy between patients.

Figure 5:
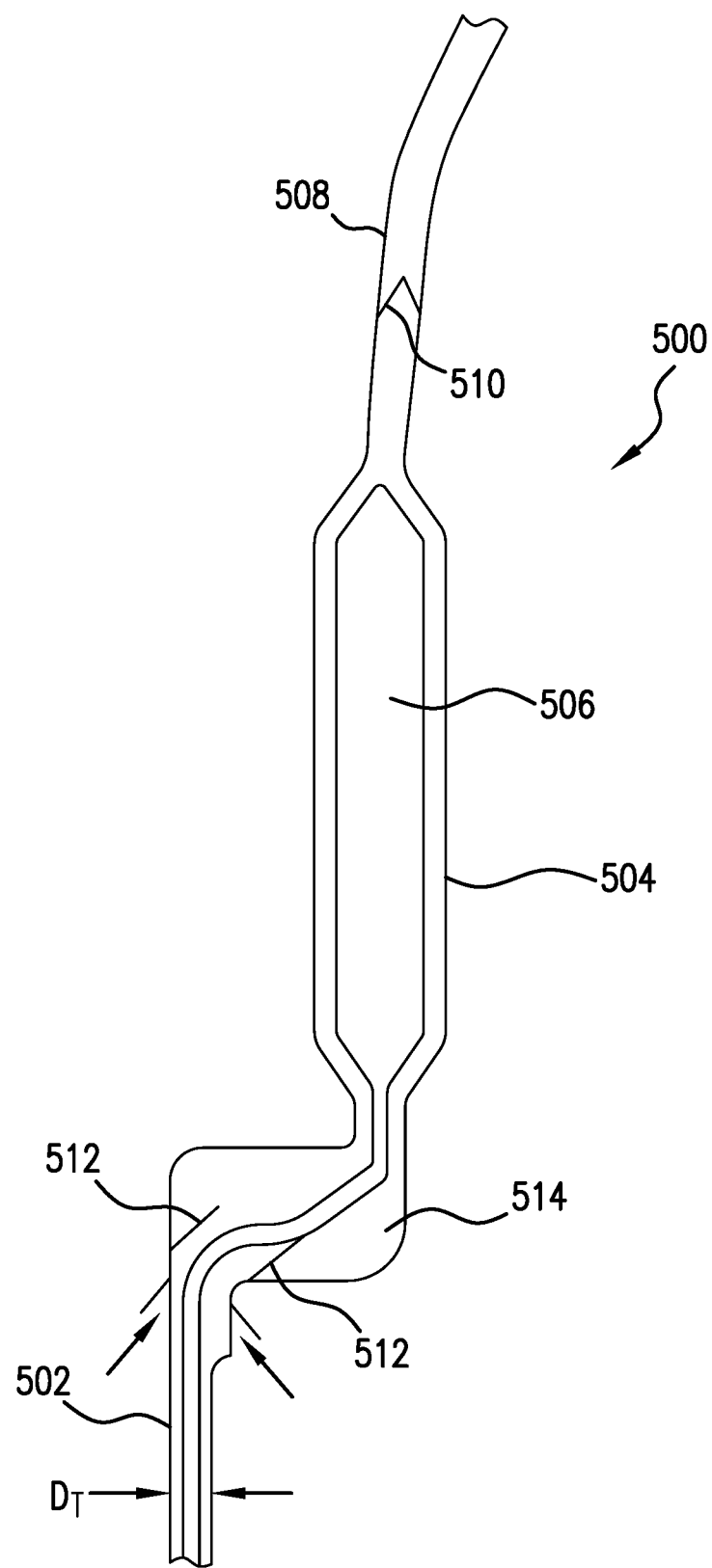
FIG. 5 is a cross-sectional schematic view of a right intravascular device according to yet another exemplary embodiment of the disclosure.

Referring now to FIG. 5, yet another embodiment of an intravascular device 500 is shown. The intravascular device 500 is a right intravascular device similar in function to the intravascular devices 100 and 200 described in connection with FIGS. 1 and 2. In the embodiment of FIG. 5, the intravascular device 500 includes an inlet valve chamber 514 with inlet valves 512 positioned therein. The inlet valve chamber 514 is coupled to a membrane chamber 504 containing a membrane balloon 506. The inlet valve chamber 514 is offset relative to the central axis of the membrane chamber 504, and the inlet valve chamber 514 may be connected to a proximal tube 502 at a location offset from the location at which the inlet valve chamber 514 is connected to the membrane chamber 504. The membrane chamber 504 is connected to a distal outlet tube 508 provided with an outlet valve 510.

The offset of the inlet valve chamber 514 may be chosen to position the inlet valve chamber 514 in such a way as to avoid occluding portions of the patient's anatomy when the intravascular device 500 is inserted within the patient's body, and/or to better accommodate a turn within the patient's circulatory system. As non-limiting examples, in a RVAD device such as device 500, the offset configuration of the inlet valve chamber 514 may avoid occlusion of the hepatic veins, while in a LVAD device, similar offset valve chamber(s) may avoid occlusion of, for example, the celiac artery. The offset may be flexible. The offset may be helical in configuration or it may be provided by a non-helical curve. The offset of the valve chamber 514 and the positioning of the intravascular device 500 may be configured so that the offset configuration of the valve chamber 514 enables the valve chamber 514 to be positioned radially away from, e.g., the hepatic vein in an RVAD device or the celiac artery in an LVAD device to avoid occlusion of those structures.

In the various embodiments of intravascular devices described in connection with FIGS. 1-5, the membrane chambers (e.g., membrane chambers 104, 204, 304, 404, and 504) and the valve chambers (e.g., valve chambers 114, 322, 324, and 514) may be configured to be collapsible to facilitate insertion and removal from the patient's body. For example, in the embodiment of FIG. 5, the valve chamber 514 may be collapsible to an overall outer diameter not substantially exceeding an outer diameter DT of the tube 502. As a non-limiting example, the inlet valve chamber 514 may include materials such as shape memory alloys or elastic structures that can be collapsed for insertion within the body, and return to an expanded configuration once in place within the patient. Likewise, the structures of the membrane chambers 104, 204, 304, 404, and 504, and the valve chambers 114 (FIG. 1), and 322, 324 (FIG. 3) may similarly be configured to be collapsed to a reduced diameter compared to an expanded configuration to facilitate insertion of the intravascular devices within the patient's body. For example, the membrane chambers 104, 204, 304, 404, and 504, and valve chambers 114, 322, and 324 may comprise materials such as shape memory alloys, elastic materials configured as a collapsible scaffold, framework, or mesh, or other materials and configurations.

Referring now to FIGS. 6 and 7, a device and procedure for inserting an intravascular device 600 within a patient's body is shown and discussed. The intravascular device 600 is placed within a deployment-retraction sheath 636. The intravascular device 600 may be placed within the deployment-retraction sheath 636 during manufacturing, during packaging, or at another time. Various components of the intravascular device 600 may be configured to be placed in a collapsed configuration to facilitate insertion of the intravascular device 600 within the deployment-retraction sheath 636. For example, as discussed above, components such as a membrane chamber (e.g., any of membrane chambers 104, 204, 304, 404, and 504) and one or more valve chambers (e.g., valve chambers 114, 322, 324, and 514) may have a collapsed configuration in which they fit within the deployment-retraction sheath 636 as shown in FIG. 6. In the exemplary embodiment of FIGS. 6 and 7, the intravascular device 600 includes a coil 660 comprising an elastic material positioned within a membrane chamber 604 in a collapsed configuration. In this collapsed configuration, the deployment retraction sheath 636 may be inserted within an anatomical structure (e.g., through an incision through bodily tissue) such as a femoral artery (in the case of a LVAD) or femoral vein (in the case of an RVAD). In other exemplary embodiments, depending on the configuration of the intravascular device 600 or needs of the patient, the intravascular device 600 may be inserted within the axillary, subclavian, or brachiocephalic artery or vein. In some exemplary embodiments, the deployment-retraction sheath 636 may include a reinforcing coil. Additional details regarding catheter structures and sheaths including similar coils can be found in U.S. Pat. No. 6,935,999, issued Aug. 30, 2017, the entire contents of which are incorporated by reference herein.

In some exemplary embodiments, prior to insertion of the deployment-retraction sheath 636, a guidewire (not shown) may first be inserted and a distal end thereof positioned in the desired anatomical location, such as the pulmonary trunk for a RVAD device or the left ventricle for a LVAD device. The deployment-retraction sheath 636 and intravascular device 600 are guided along the guidewire to the desired position.

As discussed in connection with FIG. 1, in some exemplary embodiments, the intravascular device 600 may include markers at various positions on the device to aid a practitioner in correctly locating the device within the patient using fluoroscopic visualization. For example, in one exemplary embodiment, the valves of the device, such as inlet and/or outlet valves, may include radiopaque markers to enable the practitioner to position the valves at anatomically optimal locations, as discussed above.

Once the intravascular device is correctly located within the patient's body, the deployment-retraction sheath 636 is withdrawn a certain distance. Once clear of the deployment-retraction sheath 636, components of the intravascular device 600 in a collapsed position, such as, for example, the membrane chamber 604 and valve chambers (e.g., valve chambers 114, 322, 324, and 514) may expand to their expanded configuration, e.g., as shown schematically in FIG. 7 in dashed lines. For example, in the embodiment of FIGS. 6 and 7, the coil 660 elastically expands to place the membrane chamber 604 in the expanded configuration shown in FIG. 7 as the sheath is removed from the intravascular device 600. Alternatively, the membrane chamber 604 and valve chamber(s) may be configured to expand upon command, such as by application of an electrical current or temperature differential to a shape-memory alloy. The deployment-retraction sheath 636 is withdrawn a distance sufficient to expose the valves of the intravascular device 600. Accordingly, the distance the deployment-retraction sheath is withdrawn may depend at least partly on the number and position of valves of the intravascular device 600.

Removal of the intravascular device 600 may include reversal of one or more of the insertion acts described above. For example, to remove the intravascular device 600, the deployment-retraction sheath 636 may be advanced over the components of the intravascular device 600, such as over the membrane chamber and/or valve chambers to compress the components to a diameter or size that fits within the deployment-retraction sheath 636, and the deployment-retraction sheath 636, with the intravascular device 600 positioned therein, may be withdrawn from the patient's body. When deployed, the various described membrane chambers and valve chambers possess sufficient rigidity to retain their fully deployed shapes within the patient's vasculature, which means their rigidity is sufficient to withstand intra-arterial pressures. However, these structures have may be configured to have sufficient flexibility to collapse manually when pulled through the patient's vasculature because forces exerted by the walls of more narrow blood vessels may exceed intra-arterial pressures and are sufficient to collapse these chambers as they are pulled through more distal vasculature and the access incisions through which the intravascular devices were initially inserted. Additionally, the sheath may exhibit sufficient hoop strength to cause the structures to collapse manually once pulled into the sheath.

The guidewire may be withdrawn from the patient before or after withdrawal of the deployment retraction sheath 636. Depending on the configuration of the intravascular device 600, the membrane balloon (e.g., membrane balloon 106 (FIG. 1)) and associated shaft 116 (FIG. 1) may have been inserted within the intravascular device 600 prior to insertion of the device within the patient, such as during manufacturing or packaging, or may be inserted through a hemostasis valve 638 once the intravascular device 600 is in position in the patient. For example, in an exemplary embodiment, an intravascular device without the membrane balloon 106 and shaft 116 may be inserted and positioned within the patient in the desired location to effect therapy. Once the intravascular device is in place, the membrane balloon 106 and shaft 116 are then inserted through the hemostasis valve 638 and advanced until the balloon 106 is located within the membrane chamber (e.g., membrane chamber 104 in FIG. 1).

The intravascular device 600 may be connected to a pump drive console 640. The pump drive console 640 may provide an alternating fluid pressure through the shaft 116 (FIG. 1) to the membrane balloon 106 to alternatingly inflate and deflate the membrane balloon 106 as discussed above. The timing of the inflation and deflation cycles of the pump drive console 640 may be set manually by a practitioner based on factors such as operating characteristics of the intravascular device 600 and factors related to the condition and needs of the patient.

Figure 8:
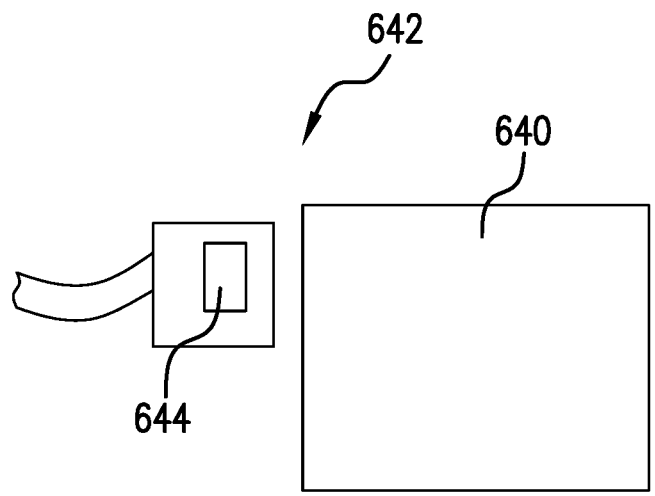
FIG. 8 is an enlarged view of the portion of the schematic of FIG. 6.

In some exemplary embodiments, the pump drive console 640 may include a system that controls the timing of the inflation and deflation cycles of the pump drive console 640 based on information received from the intravascular device 600. For example, referring now to FIG. 8, the intravascular device 600 (FIGS. 6 and 7) may include a connector assembly such as connector portion 642 comprising an identification device 644 that is configured to provide information regarding operating characteristics of the intravascular device 600 to the pump drive console 640 (FIGS. 6 and 7). The identification device 644 may comprise a passive electronic component, such as a resistor or jumper wire, or may include an electronic memory component, such as a form of non-volatile memory (e.g., EEPROM). The pump drive console 640 may be configured to read information from the identification device 644 and determine an appropriate operating mode based at least in part on the information imparted by the identification device 644. In some embodiments, information regarding the intravascular device 600 may be shared with the pump drive console using other components, such as an RFID tag on the intravascular device 600 and an RFID sensor of the pump drive console 640.

Figure 9:
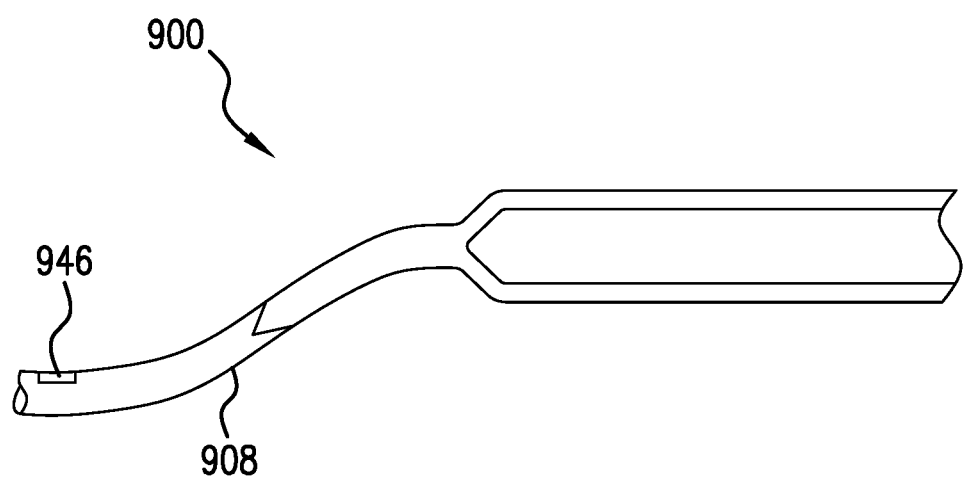
FIG. 9 is an enlarged view of the portion of an intravascular device according to an exemplary embodiment of the disclosure.

Additionally or alternatively, the intravascular device 600 may be configured to provide to the pump drive console 640 real-time information regarding the pressure conditions within the membrane chamber (e.g., membrane chamber 104 (FIG. 1)). For example, referring now to FIG. 9, a right intravascular device 900 includes a pressure transducer 946 within the outlet tube 908 and configured to detect the pulmonary pressure. The pressure transducer 946 may be, for example, a fiber-optic pressure transducer utilizing an optical cavity that changes in response to applied pressure or other optical configurations and/or components. Pressure information obtained from the pressure transducer 946 may be transmitted to the pump drive console 640 (FIGS. 6 and 7) through the connector portion 642 when the connector portion 642 is coupled with a complementary connector on the pump drive console 640. Additionally, or alternatively, blood pressure measurements can be made using a side port (not shown) of the deployment-retraction sheath 636 (FIGS. 6 and 7). Blood pressure may be measured, for example, in the superior vena cava (the in case of a RVAD) or the aorta (in the case of a LVAD). While the pressure transducer 946 is shown within the outlet tube 908, in exemplary embodiments, one or more pressure transducers may be included adjacent to intake valves and/or outlet valves, such as adjacent inlet valves 112 (FIG. 1) and outlet valve 110 (FIG. 1).

Information regarding the pressure within the membrane balloon (e.g., membrane balloon 106 in FIG. 1) may be used to control the operation of the pump drive console 640. For example, the pressure within the membrane balloon 106 may be detected by a pressure transducer within the pump drive console 640, or by a pressure transducer similar to pressure transducer 946 (FIG. 9) located within the membrane balloon 106 itself.

In an exemplary embodiment, the pump drive console 640 may control various operational characteristics such as, for example, timing of inflation and deflation events based on the pressure in the membrane balloon 106. For example, based on the pressure waveform of the membrane balloon, the pump drive console 640 can detect when the membrane balloon 106 is completely deflated, and immediately switch to inflation to re-inflate the membrane balloon 106. Additionally, or alternatively, the pump drive console 640 can detect when the pressure within the membrane balloon 106 has reached a plateau, and immediately begin deflating the membrane balloon 106.

In some exemplary embodiments, a time delay between deflation and inflation may be utilized to enhance filling and evacuation of the membrane chamber 104 (FIG. 1). For example, assuming the membrane chamber is not a perfectly rigid structure, blood flow into the membrane chamber 104 may be such that the membrane chamber 104 does not fill as quickly as the membrane balloon 106 deflates, a dwell time at maximal deflation may be used to ensure the membrane chamber 104 fills completely with blood. Similarly, in some embodiments, a dwell time at maximum inflation is used to ensure complete evacuation of the membrane chamber 104. Such dwell times may be equal or unequal based on, for example, unequal flow resistances into and out of the membrane chamber 104, and may be based on the characteristics of the intravascular device, anatomical conditions, or both.

Additionally, or alternatively, in some exemplary embodiments, the pressure of either the membrane chamber 104 or the membrane balloon 106 may be monitored by the pump drive console 640 and a change in pressure over time may be used to control inflation or deflation of the membrane balloon 106. For example, the change in pressure over time (dP/dt) is monitored, and when this value approaches zero the blood flow into or out of the membrane chamber 104 is minimal. The pump drive console 640 can use this pressure information to minimize dwell times at the inflated and deflated state, subject to the additional considerations noted above regarding the potential need for lengthened dwell times.

Additional aspects of the operation of the pump drive console 640 may be based on various factors relating to characteristics of the intravascular devices according to exemplary embodiments of the present disclosure. For example, the pump drive console 640 may include a manual setting mode which allows a practitioner to manually set timing of the inflation-deflation cycles including dwell times. Such a manual mode could also enable a practitioner to configure the pump drive console 640 to operate in a co-pulsation mode, in which the intravascular device provides pumping action in phase with the beating of the patient's heart, or a counter-pulsation mode, in which the intravascular device provides pumping action out of phase with the beating of the patient's heart. Signals representative of the action of the patient's heart may be obtained through, for example, an electrocardiogram (EKG) signal or other heart activity monitoring signal, such as a pressure signal from the pulmonary artery. In some embodiments, the pump console 640 may be configured to detect the heart activity and supplement action of the heart as necessary to maintain a particular flow rate. In other words, if the patient's heart activity is relatively weak, the pump console 640 will drive the intravascular device 600 to provide a relatively higher supplemental flow rate than if the patient's heart activity were relatively stronger. Additionally, certain functions of the pump drive console 640, such as alarms or alarm settings based on pressure conditions, user interface settings, or other settings can be optimized for use with intravascular devices according to the present disclosure.

Additionally, the inflation/deflation cycles of the pump console 640 may be asynchronous with the pulsation of the patient's heart. While the pulsatile nature of the pumping action of the intravascular device 600 is noted above, various aspects of the intravascular device 600 may be altered to provide a flow with a waveform closer to continuous flow. For example, the size and configuration of the valves and tubes of the intravascular device 600 may influence the flow from the intravascular device 600 and approximate a more consistent flow rate. As an additional example, the volume of the membrane chamber 104 (FIG. 1) and the membrane balloon 106 (FIG. 1) may be changed to alter the pumping characteristics of the intravascular device. For example, if the volume or displacement of the membrane balloon 106 is reduced, each inflation/deflation cycle of the balloon 106 pumps a smaller volume of blood. To compensate and provide the same flow rate as a device with a relatively larger membrane balloon 106, the cycle time of a complete inflation/deflation cycle may be reduced. Thus, smaller, more frequent pulses will be delivered by the intravascular device, and the smaller, more frequent pulses may more closely approximate a continuous flow from a physiological perspective. In such a system, when used in the right heart, it is not necessary to pace with the native heart rate. In addition, in the right heart, the cycling can be asynchronous.

As a non-limiting example of device sizes, a membrane balloon for use in an adult using a co-pulsation (in phase) mode, counter-pulsation (out of phase by a predetermined degree) mode, or asynchronous cycle (i.e., phase shift between the heart and the pumping membrane varies with time; an asynchronous cycle may, for example, cycle the device at a rate other than the native heart rate or may cycle the device at the patient's heart rate but with a timing that is neither co-pulsation or counter-pulsation but rather somewhere between them) may have a displacement ranging from about 25 cubic centimeters (cc) to about 50 cc per cycle. To provide smaller, more frequent flow pulses, the displacement of the membrane balloon may be reduced by, for example, 50% or more, and the cycle time of a full inflation/deflation cycle may be reduced by a corresponding (e.g., a proportional) amount. In this way, the amount of supplemented blood flow provided by the intravascular device in combination with the patient's own cardiac output maintains systemic blood flow substantially at a desired physiologic target range, although when using a smaller pumping membrane then higher rates of cycling are required to achieve the same degree of blood flow supplementation as may be achieved by a larger pumping membrane cycling at a slower rate. In one example embodiment, the balloon membrane may have a volume ranging from about 5 cc to about 20 cc, and the cycle time is reduced from a typical co- or counter-pulsation cycle and ranges, for example, from about 40% to about 90% less.

In one exemplary embodiment, the cycling rate may be generally inversely proportional to a volume of the inflatable membrane. As will be understood by those of skill in the art, variables such as the filling and emptying time of the membrane chamber would impact this proportionality.

In addition, the length and diameter of the membrane balloon may be changed while keeping the volume of the membrane balloon constant to enable, for example, use of a relatively longer, narrower membrane chamber, which may improve blood flow around the device. Moreover, multiple membrane balloons within a single membrane chamber, or multiple chambers each with one or more respective balloons, may be used.

In accordance with one aspect of the present disclosure, connection of the connector assembly, e.g., connector portion 642 with identification device 644 to the pump console may cause the pump console to automatically switch between operational modes, for example, from a first general operational mode to a second operational mode specific to intravascular devices. In such an embodiment, when switching to the second operational mode, the pump console may display operational settings associated with the intravascular device. Examples of such operational settings include, but are not limited to, alarm settings, detection settings, alarm conditions, device cycle triggering, device cycle timing, and user interface settings.

Figure 10:
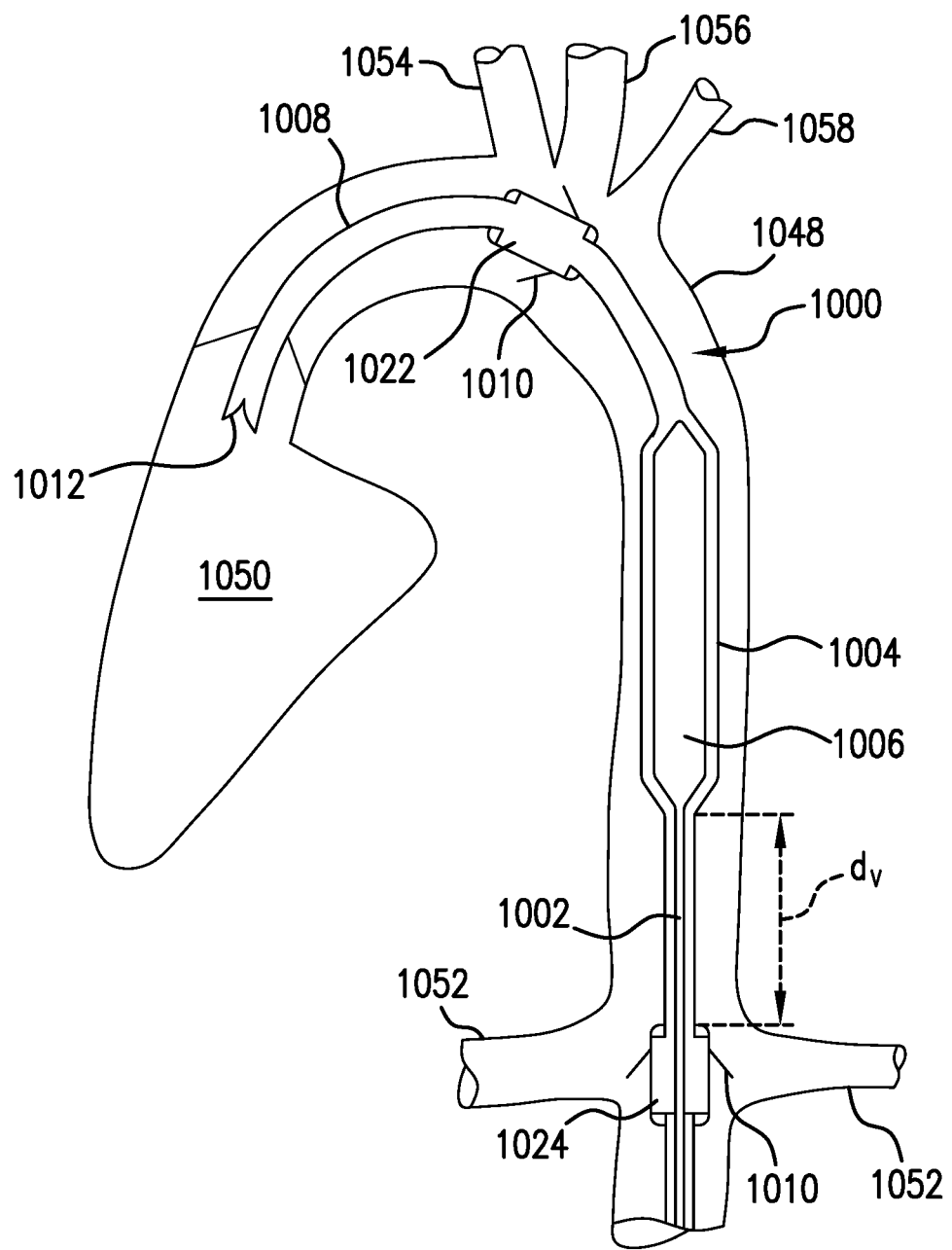
FIG. 10 is schematic side view of an intravascular device shown positioned within a portion of a patient's left heart according to an exemplary embodiment of the disclosure.

Referring now to FIG. 10, an intravascular device 1000 according to an exemplary embodiment is shown positioned within a schematic drawing of an arterial structure 1048 of a patient's left heart and aorta. This exemplary embodiment may be characterized as a left heart intravascular device. The intravascular device 1000 includes a membrane chamber 1004 within which a membrane balloon 1006 is disposed. The intravascular device 1000 includes a one-way inlet valve 1012 positioned at a distal end of a distal tube 1008. A distal end of the distal tube 1008 extends into the patient's left ventricle 1050. Outlet valves 1010 are disposed in valve chambers 1022 and 1024 positioned distal to and proximal to the membrane chamber 1004, respectively. The valve chamber 1024 is positioned along a tube 1002 and is located a distance dv from the membrane chamber 1004. The distance dv may be chosen such that the valve chamber 1024 and the associated outlet valve 1010 is located adjacent to a renal artery 1052. Such positioning of the valve chamber 1024 may facilitate perfusion of blood expelled from the outlet valve 1010 into the renal artery 1052. Positioning the valve chamber 1024 adjacent the renal artery 1052 may be facilitated by, e.g., radiopaque markers such as radiopaque markers 117 (FIG. 1).

The location of the valve chamber 1022 distal to the chamber 1004 may be chosen such that the valve chamber 1022 is positioned adjacent one or more of the brachiocephalic artery 1054, the left common carotid artery 1056, and the left subclavian artery 1058. Stated differently, when the distal end of the distal tube 1008 is positioned in a target position (e.g., within the left ventricle 1050), one outlet valve 1010 is positioned adjacent the arteries in the aortic arch (e.g., the brachiocephalic artery 1054, the left common carotid artery 1056, and the left subclavian artery 1058), while the other outlet valve 1010 is positioned adjacent the renal arteries 1052. Positioning the valve chamber 1022 adjacent, e.g., the common carotid arteries, may facilitate cerebral perfusion of blood expelled from the outlet valve 1010 associated with the valve chamber 1022. Positioning of the valve chamber 1022 may be facilitated by radiopaque markers, such as radiopaque markers 117 (FIG. 1). In some exemplary embodiments, the valve chamber 1022 may be positioned closer to the distal end of the distal tube 1008 than the position shown in FIG. 11, and the direction of the outlet valve 1010 may be reversed to direct blood flow toward the brachiocephalic artery 1054, the left common carotid artery 1056, and the left subclavian artery 1058.

Figure 11:
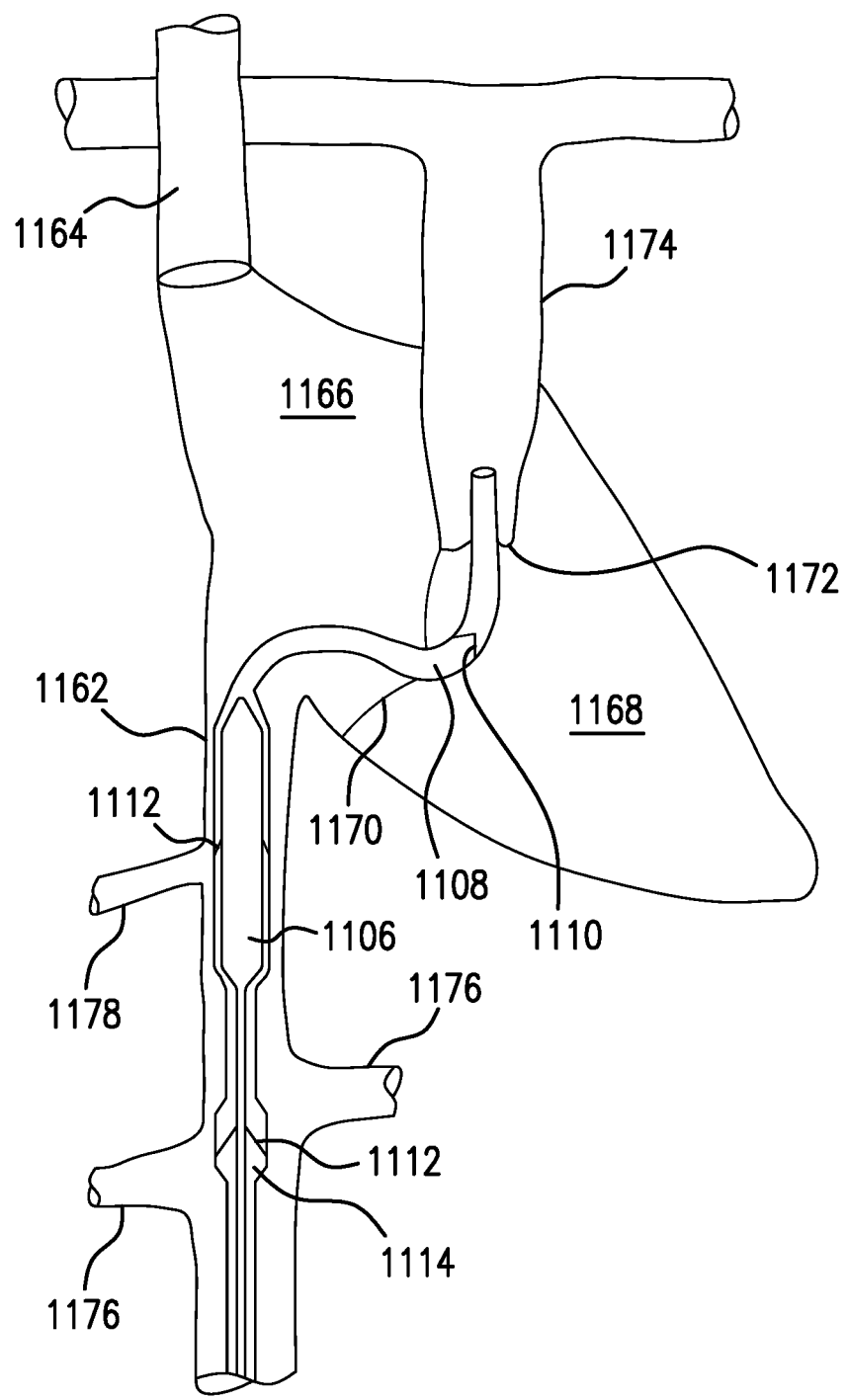
FIG. 11 is a schematic side view of an intravascular device shown positioned within a portion of a patient's right heart according to another exemplary embodiment of the disclosure.

Referring now to FIG. 11, an intravascular device 1100 according to another embodiment of the disclosure is shown positioned within a venous structure of a patient, such as a portion of the patient's right heart 1160 and inferior vena cava. This exemplary embodiment may be characterized as a right heart intravascular device. The intravascular device 1100 includes a membrane chamber 1104 within which is positioned a membrane balloon 1106. A distal tube 1108 with a one-way outlet valve 1110 extends distally from the membrane chamber 1104. In the embodiment of FIG. 11, the membrane chamber 1104 is positioned within the inferior vena cava (IVC) 1162. However, as non-liming examples of alternative configurations, the present disclosure contemplates positioning the membrane chamber 1104 within the superior vena cava 1164, the right atrium 1166, or the right ventricle 1168. To facilitate such positioning, configurations of the intravascular device 1100 may feature different shapes and sizes of the membrane chamber 1104, different lengths of the distal tube 1108, etc. In the embodiment of FIG. 11, the distal tube 1108 extends from the membrane chamber 1104 in the IVC, through the right atrium 1166 and past the tricuspid valve 1170, through the left ventricle 1168 and past the pulmonary valve 1172 and into the pulmonary artery 1174.

The intravascular device 1100 includes an inlet valve 1112 positioned in an inlet valve chamber 1114. The inlet valve chamber 1114 is positioned proximal to the membrane chamber 1104, and the position of the inlet valve chamber 1114 may be chosen to locate the inlet valve 1112 proximate a venous structure of the patient, such as renal veins 1176. In addition, in the exemplary embodiment of FIG. 11, an additional inlet valve 1112 may be positioned on the membrane chamber 1104, and the additional inlet valve 1112 may be located proximal another venous structure of the patient, such as a hepatic vein 1178.

Stated another way, the device 1100 may be configured such that when the distal tube 1108 is positioned within a target position within the pulmonary artery 1174, the inlet valves 1112 may be positioned adjacent anatomical structures such as, for example, the hepatic vein 1178, one or more renal veins (not shown), or other anatomical structures.

The procedures discussed above with regard to FIGS. 10 and 11 are not necessarily exclusive of one another. That is, it is possible to use a left heart intravascular device and a right heart intravascular device, as described and embodied herein, together to provide bi-ventricular support. Thus, a system for providing bi-ventricular support may include both left and right heart intravascular devices. The system may be used with a single pump console or two pump consoles.

Figure 12A:
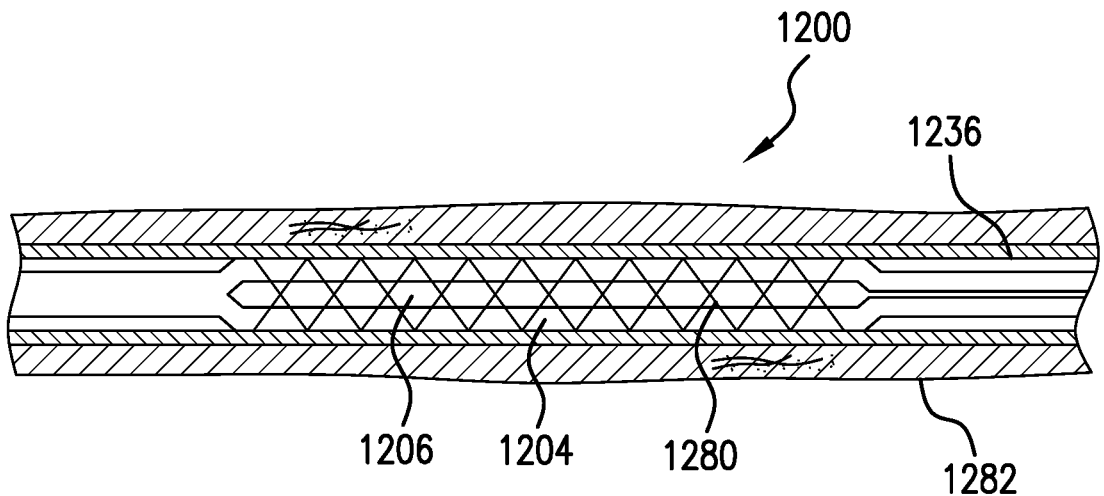
FIG. 12A is a schematic side view of an intravascular device in a compressed state within an insertion/retraction sheath according to an embodiment of the disclosure.
Figure 12B:
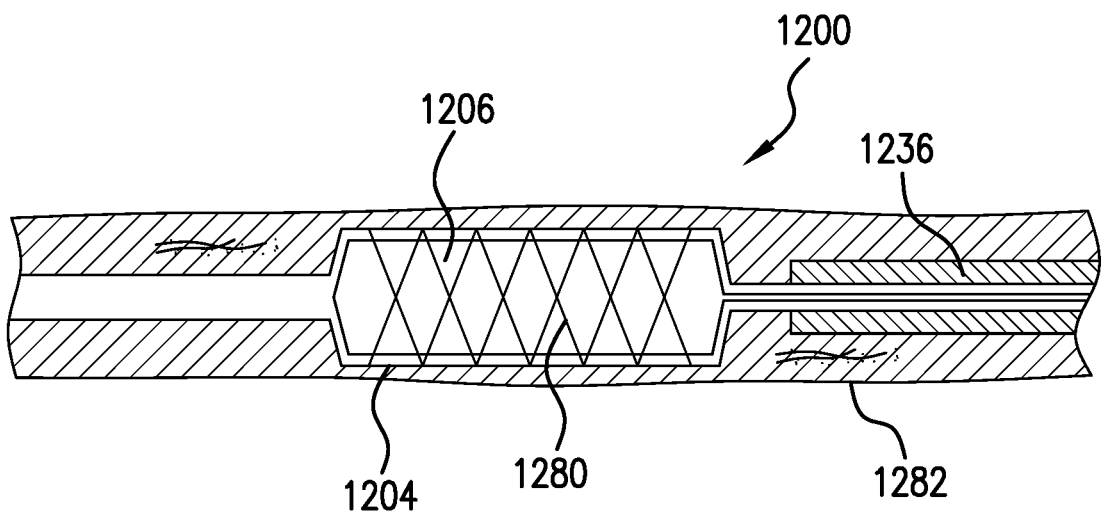
FIG. 12B is a schematic side view of the intravascular device of FIG. 12A in an expanded state partially removed from the insertion/retraction sheath.

FIGS. 12A and 12B illustrate an exemplary embodiment of an expanding chamber 1204 of an intravascular device 1200. In the embodiment of FIG. 12A, the chamber 1204 includes a mesh structure 1280, and the chamber 1204 and mesh structure 1280 are compressed within an insertion/retraction sheath 1236 that is inserted within a blood vessel 1282 of a patient. A membrane balloon 1206 within the chamber 1204 is in a deflated state in FIG. 12A. Once the chamber 1204 is advanced to the desired location, the insertion/retraction sheath 1236 is withdrawn as discussed in connection with FIGS. 6 and 7, and the mesh structure 1280 expands the chamber within the blood vessel 1282, as shown in FIG. 12B. The mesh structure 1280 may comprise, without limitation, elastic materials such as metals or polymers, shape memory materials such as metals or polymers, composite materials, or other materials, as discussed above. Once the chamber 1204 is expanded, the balloon membrane 1206 may be cyclically inflated and deflated to provide pumping action as discussed generally in the embodiments above.

Ventricular-assist devices according to the present disclosure provide advantages over previous devices. For example, intravascular devices according to the disclosure provide improved interactions with a patient's anatomy, such as avoiding occlusion of the valves of the intravascular devices by anatomical structures, and positioning the valves of the device in chosen areas to improve perfusion of blood expelled from the intravascular device. Additionally, pump drive consoles according to embodiments of the disclosure feature operating configurations and algorithms that enhance (e.g., maximize) effectiveness of intravascular devices.

It is to be understood that the particular examples and embodiments set forth herein are non-limiting, and modifications to structure, dimensions, materials, and methodologies may be made without departing from the scope of the present teachings. While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. An intravascular device for pumping blood, comprising:
   a catheter comprising a membrane chamber located between a proximal end and a distal end of the catheter, wherein following intravascular insertion the membrane chamber is moveable between a contracted configuration and an expanded configuration that has a first diameter;
   an inflatable membrane disposed within the membrane chamber, wherein the membrane chamber comprises a chamber wall free of valves;
   a valve chamber separate from the membrane chamber, wherein the valve chamber has a second diameter that is smaller than the first diameter of the membrane chamber;
   a first one-way valve configured to permit blood flow in a first direction;
   a second one-way valve configured to permit blood flow in the first direction, the second one-way valve positioned distal to the membrane chamber, wherein the second one-way valve is configured as an inlet valve formed in the distal end of the catheter, and wherein the first one-way valve is configured as an outlet valve and is positioned between the membrane chamber and the proximal end of the catheter; and
   a third one-way valve positioned between the second one-way valve and the membrane chamber, wherein the third one-way valve is configured to permit blood flow in a second direction opposite to the first direction.

2. The device claim 1, wherein one of the first and second one-way valves forms part of or is located within the valve chamber.

3. The device of claim 2, further comprising a second valve chamber separate from the membrane chamber, wherein each of the first and second one-way valves forms part of or is located within a respective one of the valve chambers.

4. The device of claim 3, wherein at least one valve chamber has a profile, when viewed along a lengthwise direction of the device, that is smaller than a profile of the membrane chamber, when viewed along the lengthwise direction of the device.

5. The device of claim 2, wherein the valve chamber has a profile, when viewed along a lengthwise direction of the device, that is smaller than a profile of the membrane chamber, when viewed along the lengthwise direction of the device.

6. The device of claim 3, wherein the catheter further comprises first and second tube portions that extend proximally and distally from the membrane chamber, respectively, and wherein at least one valve chamber has a profile, when viewed along a lengthwise direction of the device, equal to or greater than a profile of the tube portions of the catheter, when viewed along the lengthwise direction of the device.

7. The device of claim 1, wherein at least one of the first and second one-way valves is located on the device so as to be positioned adjacent to at least one of a left common carotid artery, a right common carotid artery, and a renal artery during use.

8. The device of claim 1, wherein at least one of the first and second one-way valves is located on the device so as to be positioned in a pulmonary artery during use.

9. The device of claim 1, wherein at least one of the first and second one-way valves is located on the device so as to be positioned adjacent to at least one of a renal vein and a hepatic vein when the device is positioned within a patient's heart for left-heart support.

10. The device of claim 1, wherein the second one-way valve is disposed within a valve chamber formed as an inlet tube connected to the membrane chamber.

11. The device of claim 1, wherein the first one-way valve is disposed within a valve chamber formed as an outlet tube connected to the membrane chamber.

12. The device of claim 1, wherein a marker is associated with at least one of the first and second one-way valves to facilitate positioning of the device via fluoroscopic imaging.

13. The device of claim 3, wherein a central axis of the second valve chamber is offset from a longitudinal axis of the catheter.

14. A system for pumping blood, comprising:
    an intravascular device according to claim 1; and
    a connector assembly configured to connect to the intravascular device and to a pump console and configured to allow settings on the pump console to be altered for use with the intravascular device.

15. The device of claim 1, wherein the valve chamber is located between and in fluid communication with the catheter and the membrane chamber.

16. An intravascular device for pumping blood, comprising:
    a catheter comprising a membrane chamber located between a proximal end and a distal end of the catheter, wherein following intravascular insertion the membrane chamber is moveable between a contracted configuration and an expanded configuration that has a first diameter;
    an inflatable membrane disposed within the membrane chamber, wherein the membrane chamber comprises a chamber wall having a first diameter and that is free of valves;
    a first valve chamber separate from the membrane chamber, wherein the first valve chamber has a second diameter that is smaller than the first diameter of the chamber wall of the membrane chamber;
    a first one-way valve configured to permit blood flow in a first direction, wherein the first one-way valve is disposed within the first valve chamber;
    a second valve chamber separate from the membrane chamber, wherein the second valve chamber has a third diameter that is smaller than the first diameter of the chamber wall of the membrane chamber; and
    a second one-way valve configured to permit blood flow in a second direction, wherein the second one-way valve is disposed within the second valve chamber.

17. The device of claim 16, wherein the second valve chamber is adjacent the membrane chamber and the first valve chamber is not adjacent to the membrane chamber.

* * * * *